United States Patent
Pratap et al.

(10) Patent No.: US 7,635,779 B2
(45) Date of Patent: Dec. 22, 2009

(54) OXY SUBSTITUTED FLAVONES AS ANTIHYPERGLYCEMIC AND ANTIDYSLIPIDEMIC AGENTS

(75) Inventors: Ram Pratap, Lucknow (IN); Mavurapu Satyanarayana, Lucknow (IN); Chandeshwar Nath, Lucknow (IN); Ram Raghubir, Lucknow (IN); Anju Puri, Lucknow (IN); Ramesh Chander, Lucknow (IN); Priti Tiwari, Lucknow (IN); Brajendra Kumar Tripathi, Lucknow (IN); Arvind Kumar Srivastava, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 322 days.

(21) Appl. No.: 11/052,833

(22) Filed: Feb. 9, 2005

(65) Prior Publication Data

US 2006/0178373 A1   Aug. 10, 2006

(30) Foreign Application Priority Data

Oct. 15, 2004  (IN)  ................. 2026/DEL/2004

(51) Int. Cl.
*C07D 311/30*  (2006.01)
(52) U.S. Cl. .................................................. 549/403
(58) Field of Classification Search ............... 514/456; 549/403
See application file for complete search history.

(56) References Cited

U.S. PATENT DOCUMENTS 4,889,941 A * 12/1989 Wu et al. ..................... 549/403

OTHER PUBLICATIONS

Wu et al., J. Med. Chem. vol. 35(19), pp. 3519-3525.*

* cited by examiner

*Primary Examiner*—Taofiq A Solola
(74) *Attorney, Agent, or Firm*—Harold L. Novick; Ari G. Zytcer; The Nath Law Group

(57) ABSTRACT

The present invention provides novel substituted flavone derivatives which exhibit anti-hyperglycemic and antidyslipedemic activity. The invention also provides a method for controlling type II diabetes and associated hyperlipidemic conditions in a mammal by administering compound of the present invention and compositions containing these derivatives.

2 Claims, 1 Drawing Sheet

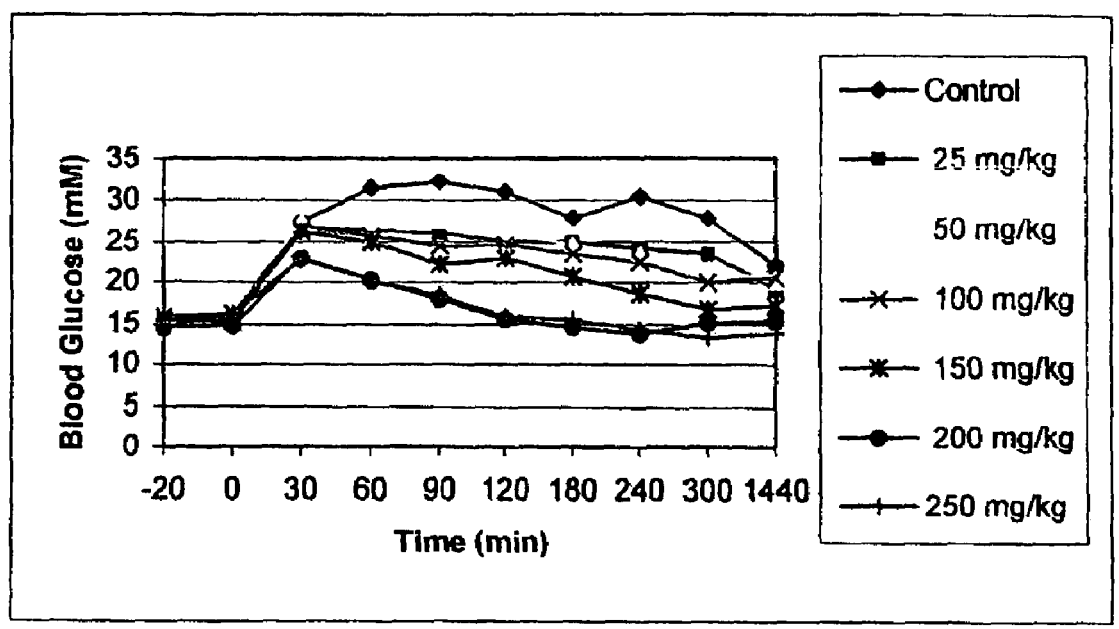

OXY SUBSTITUTED FLAVONES AS ANTIHYPERGLYCEMIC AND ANTIDYSLIPIDEMIC AGENTS

FIELD OF INVENTION

The present invention relates to synthesis of suitably substituted flavone derivatives which exhibit pronounced antihyperglycemic activity in conjunction with antidyslipedemic activity. More particularly the invention relates to synthesis of compounds having formula I and pharmaceutical composition containing these derivatives, as described in the following description.

BACKGROUND OF THE INVENTION AND PRIOR ART

Type II insulin resistant diabetes mellitus accounts for 90-95% of all diabetes. Changed sedentary life style has contributed towards affliction of the disease to adult population also. The main force driving this increasing incidence is a staggering increase in obesity, the single most important contributor to the pathogenesis of diabetes mellitus. Prolonged disease condition leads to chronic macrovascular complications such as retinopathy and nephropathy. The disease is collectively referred, as metabolic syndrome encompasses type II diabetes and common constellation of closely linked clinical features. Characteristic factors include insulin resistance per se, obesity, hypertension and a common form of dyslipidemia and low high-density lipoprotein cholesterol. Metabolic syndrome is associated with marked increased incidence of coronary, cerebral and peripheral artery disease [Executive summary of the third report of the National Cholesterol Program Expert Panel on detection, evaluation and treatment of high blood cholesterol in adults (2001), J. Am. Med. Asso. 285, 2486-2496.].

The role of peripheral and hepatic insulin resistance in the pathogenesis of diabetes mellitus is undisputed. Insulin resistance can be due to multiple defects in signal transduction such as impaired activation of insulin receptor-tyrosine kinase and reduced activation of insulin-stimulated phosphatidyl inositol-3-hydroxy kinase. The resistance of insulin due to diet-induced obesity [Elchebly, M. et al. (1999), Science, 283, 1544.] has given the critical role of obesity in the development of insulin resistance and other features of the metabolic syndrome. Successful approaches attenuating appetite and/or enhancing energy expenditure will prove of great benefit in preventing and treating type II diabetes. Abnormalities of fatty acid metabolism are increasingly recognized as key components of the pathogenesis of the metabolic syndrome and type II diabetes. A critical player in potentiating the promoting effect of hyperinsulinaemia on hepatic lipid accumulation is the anabolic transcription factor SREBP-1, which upregulates genes such as that for fatty acid synthase [Shimomura, I. et al. (2000), Mol. Cell, 6, 77-86.]. These observations support a unified "lipotoxicity" hypothesis, which states that metabolic syndrome and type II diabetes can be caused by the accumulation of triglycerides and long chain fatty-acyl-CoA in liver and muscle. The third causal factor of metabolic syndrome is oxidative stress. Excess levels of oxygen in the living body can also pose a serious health threat; the so-called oxygen toxicity is brought about by oxygen species such as hydrogen peroxide and oxy radicals and damage living tissue. The active oxygen species are associated with diabetes mellitus and are destructive towards various tissues as occurring in diabetes mellitus. There have been many reports discussing relationships between peroxidation and diseases such as diabetes mellitus, atherosclerosis and myocardial ischemia in terms of radical oxidation. Glucose is oxidized under oxidative stress to highly reactive species, which ultimately reacts with proteins. Glucose, like other alpha hydroxy aldehydes, can enolize and thereby reduce molecular oxygen under physiological conditions, catalyzed by transition metals, yielding alpha keto aldehydes and oxidizing intermediates. These secondary compounds are more reactive than monosaccharides and can react with proteins to form cross-linked Mallard products (Simon P. Wolff et al. (1991); Free Radical Biology and Medicine, 10, 339-352.).

Oxidative stress also modifies lipids. Like glucose, LDL also undergoes oxidative modification to form modified LDL (oxidized LDL). The actual oxidation process is believed to begin with lipid peroxidation, followed by fragmentation to give short chain aldehydes. These aldehydes in turn react with the lysine residues of apo-B, creating a new epitope, which is recognized by the scavenger receptor of macrophages. During this same process, lecithin is converted to lysolecithin, which is a selective chemotactic agent for monocytes. The monocytes enter the subendothelium and undergo a phenotypic change to a macrophage, which avidly take up the oxidized LDL via the scavenger receptor. The uptake of oxidized LDL continues until the macrophage is so engorged with cholesteryl esters that it transforms into a foam cell. Groups of these foam cells constitute a fatty streak, the earliest hallmark of atherosclerosis. By inhibiting the oxidation of LDL, it is hoped that the modification of apo B and the production of chemotactic lysolecithin can be prevented and in turn the atherosclerosis.

At present, therapy for type II diabetes relies mainly on several approaches intended to reduce the hyperglycemia itself: sulphonylureas which increase insulin secretion from pancreatic beta cells; metformin which acts to reduce hepatic glucose production, peroxisome proliferator activated receptor-γ agonists which enhance insulin action and α-glucosidase inhibitors which interfere with gut glucose absorption. These therapies have limited efficacy, limited tolerability and mechanism-based toxicity. Of particular concern is the tendency for most treatments to enhance weight gain. A problem particular to the sulphonylureas is that many patients who respond initially become refractory to treatment overtime.

The increasing prevalence of obesity and its associated comorbidities including type II diabetes and related cardiovascular disorders has stimulated efforts to develop effective new approaches in the treatment of this condition. While most therapeutic approaches involve altering the balance of metabolic energy by reducing energy intake, an alternative approach for the management of obesity is to affect an increase in the rate of energy expenditure. In 1984, compounds of the phenethanolamine class as shown below having thermogenic properties in rodents were first disclosed. Despite their structural similarity to known $\beta_1$ and $\beta_2$ adrenoceptor ligands, pharmacological studies indicated that these compounds stimulated a third or 'atypical' β-adrenergic receptor (β-AR) that is now described as $\beta_3$-AR. $\beta_3$ agonist also increased insulin sensitivity and glucose utilization. Later studies suggested that Tyr 64 Arg $\beta_3$-AR mutation in the human population plays a role in the development of diabetes mellitus and/or obesity in some individuals possessing this genetic variant [Turner, N. C.; (1996), DDT, 1, 109-116].

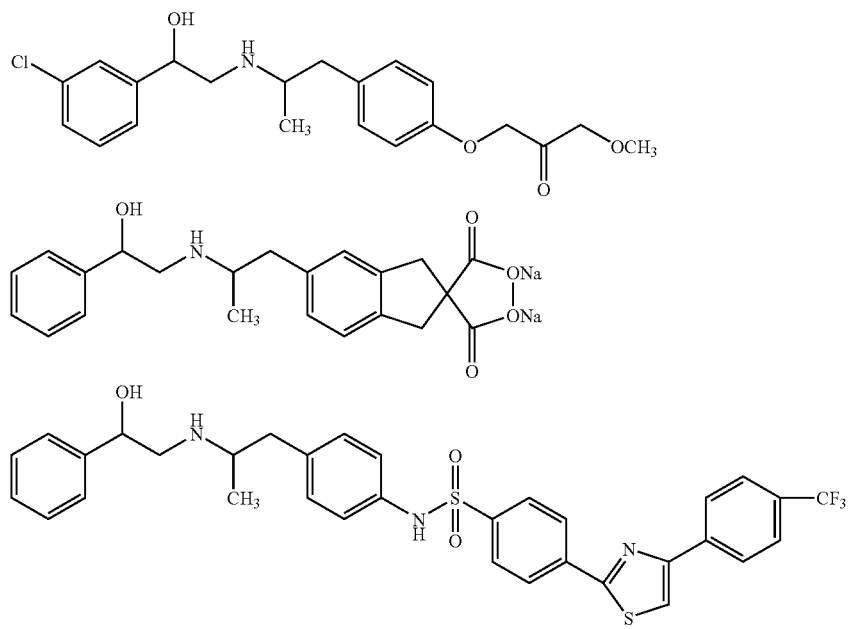

A family of transcription factors, known as PPAR-γ plays a crucial role in regulating the storage and catabolism of dietary energy producing materials. There are three PPAR subtypes that are the products of distinct genes and are commonly designated as PPPAR α, γ and δ. PPAR-γ affect body weight through regulation of fatty acid catabolism or energy expenditure. PPAR-γ expressed mainly in adipose tissue plays a pivotal role in regulation of glucose and lipid homeostasis [Willson, T. M. et al. (2000), J. Med. Chem. 43, 527-550].

Troglitazone effectively reduces hyperglycemia, hyperinsulinaemia and hypertriglyceridemia in patients with type II diabetes. The mechanism of pharmacological effects has been shown to involve increased insulin sensitivity effects in skeletal muscle, liver and adipose tissue via the activation of PPAR-γ. As vitamin-E analogue, troglitazone has been demonstrated to be an effective antioxidant; oxidative ring opening and subsequent quinone metabolite formation is believed to be the cause of hepatotoxicity and withdrawal of the drug [Kan He, et al. (2001), Biochemical Pharmacology, 62, 191-198.]. This has led to the modification and resulted in several new molecules.

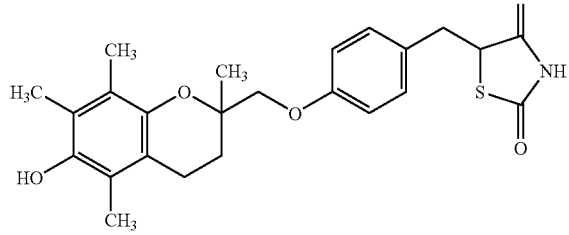

Troglitazone

-continued

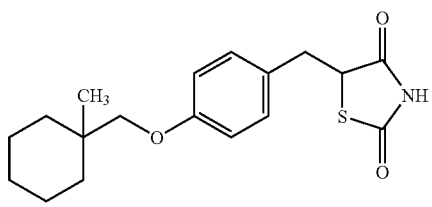

Ciglitzone

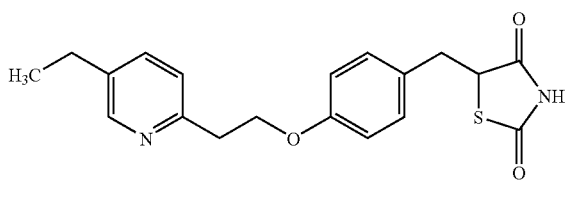

Pioglitazone

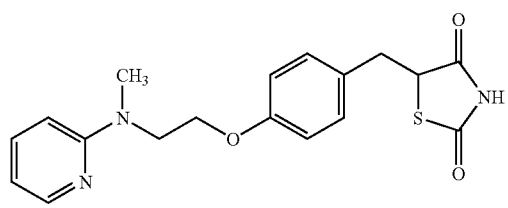

Rosiglitazone

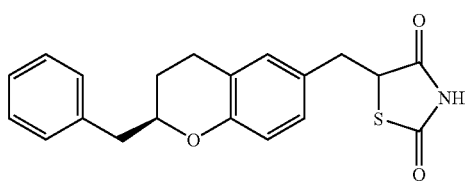

Englitazone

-continued

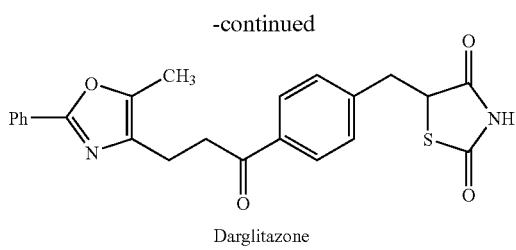

Darglitazone

Grafting of pharmacophores on systems own or very close metabolites may exhibit some times undesired effects. For example first generation of statins though derived from fungal metabolite, is very close analogue of mevalonic acid and therefore function as HMG-CoA reductase inhibitors, block mevalonate production which is involved in cholesterol biosynthesis and hence cholesterol synthesis is inhibited in the cell. Mevalonate is a common precursor for all isoprenoids such as ubiquinones (co enzyme Q 10), the dolichols, and isopentenyl tRNA etc. Therefore, there is a decrease in the synthesis of non-sterol constituents, which may contribute significantly to the side effects, observed with HMG-CoA reductase inhibitors. Similarly in designing of troglitazone, vitamin-E component was used which metabolized to quinonoid intermediate after one electron oxidation. This intermediate is speculated to be the cause of toxicity of troglitazone.

Flavonoids are among the most ubiquitous groups of polyphenolic compounds in foods of plant origin. As integral constituents of the diet, they may exert a wide range of beneficial effects on human health. Flavonoids produce such biological effects through their free radical scavenging antioxidant activities and metal ion chelating abilities. (Cotelle, N. et al, Free Rad. Biol. Med. 1992, 13, 211.). These properties led us to utilize flavones for the synthesis of hybrid molecules as antidiabetic and antidyslipidemic agents by substitution with thermogenic as well as insulin sensitizing pharmacophores.

OBJECTS OF THE PRESENT INVENTION

The main objective of the present invention is to provide a substituted flavone derivative of formula I or a pharmaceutically acceptable salt thereof.

Another object of the present invention is to provide a pharmaceutical composition containing these flavone derivatives and a pharmaceutically acceptable carrier or diluent thereof.

Yet another object of the present invention is to provide a pharmaceutical composition containing the flavone derivatives of the present invention along with a lipid lowering agent and/or a sugar lowering agent.

Still another object of the present invention is to provide processes for preparation of compound of formula I.

Yet another object of the present invention is to provide a method for treating type II diabetes and associated hyperlipidemic conditions in a mammal by administering a pharmaceutically acceptable amount of compound I optionally with other diabetic and lipid lowering agents.

Still another object of the present invention is to provide a method of treating macrovascular conditions such as retinopathy and nephropathy in mammals by administering a pharmaceutically acceptable amount of the compound I optionally with other diabetic and lipid lowering agents.

SUMMARY OF THE INVENTION

Accordingly, the present invention provides novel flavone derivatives of formula I which exhibit antihyperglycemic and antidyslipedemic activity. The invention also provides a method for controlling 'type II' diabetes and associated hyperlipidemic conditions in a mammal by administering these compounds and compositions containing these derivatives.

DESCRIPTION OF THE DRAWING

The FIGURE is a dose dependent curve of 34 on sucrose challenged streptozotocin-induced diabetic rats.

DETAILED DESCRIPTION OF THE INVENTION

The present invention provides novel flavone derivatives, which exhibits antidiabetic and antidyslipidemic activities in different model systems. More particularly, this invention relates to compounds having the formula (I) and pharmaceutically acceptable salts thereof. Where in the groups $R^1$, $R^2$, $R^3$, $R^4$, $R^5$ and $R^6$ are as herein after defined.

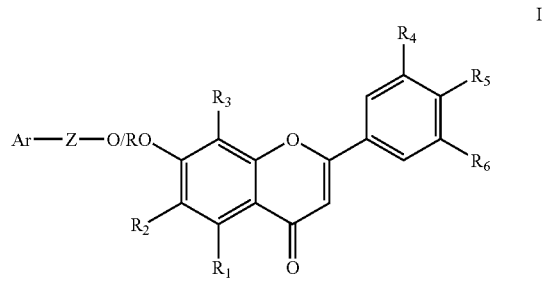

Wherein $R^1$, $R^2$ and $R^3$ are selected from hydrogen, methyl or iso pentenyl;

$R^4$, $R^5$ and $R^6$ are selected from H, OH, O-alkyl, O-phenyl, O-substituted phenyl or combination thereof;

R is propanolamine wherein amino groups are selected from t-butyl amine, n-butyl amine, i-butyl amine, i-propyl amine, 4-phenyl piperazine-1-yl amine, 4-(2-methoxy phenyl)-piperazin-1-yl amine, and 3,4-dimethoxy phenethyl amine;

Where Z is an alkane chain having 1 to 3 carbon atoms;

Ar is thiazolidinedione methylene phenol

Another embodiment of the present invention provides a pharmaceutical composition comprising the compound of formula I and pharmaceutically acceptable quantities of a conventional pharmaceutically acceptable carrier or diluent thereof.

Yet another embodiment of the present invention provides a pharmaceutical composition comprising the compound of formula I along with pharmaceutically acceptable quantities of conventional lipid lowering agents and/or conventional sugar lowering agents.

Yet another embodiment of the present invention provides a method for treating type II diabetes and associated hyperlipidemic conditions in mammals by administering a pharmaceutically effective amount of compound of formula I, optionally with other diabetic and lipid lowering agents.

Yet another embodiment of the present invention provides a method for treating type II diabetes and associated hyperlipidemic conditions in mammals by administering a pharmaceutically effective amount of compound of formula (34), optionally with other conventional diabetic and lipid lowering agents.

Yet another embodiment of the present invention provides a method for treating type II diabetes and associated hyperlipidemic conditions in mammals by administering a pharmaceutically effective amount of compound of formula (49), optionally with other conventional diabetic and lipid lowering agents.

Yet another embodiment of the present invention provides a method for treating type II diabetes and associated hyperlipidemic conditions in mammals by administering a pharmaceutically effective amount of compound of formula (65), optionally with other conventional diabetic and lipid lowering agents.

Yet another embodiment of the present invention provides a method of treating macrovascular conditions such as retinopathy and nephropathy in mammals by administering a pharmaceutically effective amount of the compound of formula I, optionally with other conventional diabetic and lipid lowering agents.

Yet another embodiment of the present invention provides a method of treating macrovascular conditions such as retinopathy and nephropathy in mammals by administering a pharmaceutically effective amount of the compound of formula (34), optionally with other conventional diabetic and lipid lowering agents.

Yet another embodiment of the present invention provides a method of treating macrovascular conditions such as retinopathy and nephropathy in mammals by administering a pharmaceutically effective amount of the compound of formula (49), optionally with other conventional diabetic and lipid lowering agents.

Yet another embodiment of the present invention provides a method of treating macrovascular conditions such as retinopathy and nephropathy in mammals by administering a pharmaceutically effective amount of the compound of formula (65), optionally with other conventional diabetic and lipid lowering agents.

Yet another embodiment of the present invention provides the range of pharmaceutically effective dose of 50-250 mg/Kg body weight of the compound optionally with other diabetic and lipid lowering agents, to be administered in mammals.

Still another embodiment of the present invention provides a compound of formula (34).

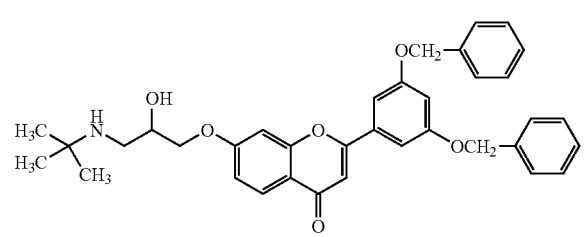

34

Yet another embodiment of the present invention provides a compound of formula (49).

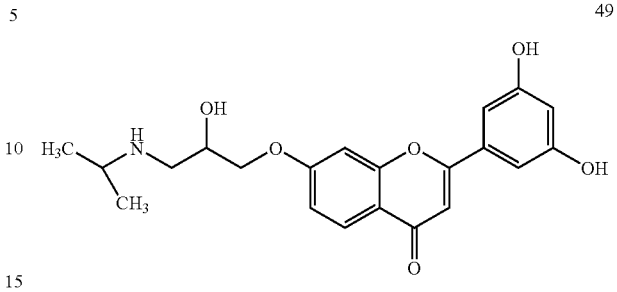

49

Yet another embodiment of the present invention provides a compound of formula (65).

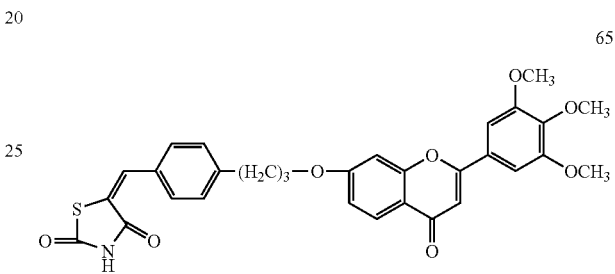

65

Still another embodiment of the present invention provides a process for preparing a compound of formula I, comprising the steps of:
(i) reacting dihydroxy acetophenone with substituted ethyl benzoate in the presence of lithiumhexamethyldisilazane in dry tetrahydrofurane to obtain 1,3-dibenzoyl methanes;
(ii) reacting 1,3-dibenzoyl methanes obtained in step (i) with Dowex-$H^+$ in 2-propanol at reflux to yield respective flavone;
(iii) reacting substituted hydroxy flavone obtained in step (ii) with epichlorohydrin in presence of sodium hydride in dry dimethyl formamide;
(iv) heating 2,3-epoxy-propoxy-flavones as obtained in step (iii) under reflux, with amines in methanol to yield propanolamines; and
(v) undergoing debenzylation of dibenzylated flavone derived propalomines as obtained in step (iv) using catalytic hydrogenation process to yield corresponding dihydroxy flavone derived propanolamines.

Yet another embodiment of the present invention provides a process for preparing a compound of formula I, comprising the steps of:
(i) reacting substituted hydroxy flavones with dibromo alkane in presence of $K_2CO_3$ and dry dimethyl formamide at room temperature to obtain bromo alkoxy flavones;
(ii) reacting bromo alkoxy flavone obtained in step (i) with 4-(Thiazolidin-2,4-dione-5-ylidinemethyl)-phenol in dry dimethyl formamide at room temperature to yield corresponding flavones.

Still another embodiment of the present invention provides a compound having formula I or a pharmaceutically acceptable salt thereof, wherein the representative compounds are:
a) 7-(3-tert-Butylamino-2-hydroxy-propoxy)-3',5'-dibenzyloxy-flavone (34);

b) 3',5'-Dibenzyloxy-7-(2-hydroxy-3-iso-propylamino-propoxy)-flavone (35);
c) 3',5'-Dibenzyloxy-7-[2-hydroxy-3-(4-phenylpiperazin-1-yl)-propoxy]-flavone (36);
d) 7-(3-tert-Butylamino-2-hydroxy-propoxy)-3',4'-dibenzyloxy-flavone (37);
e) 3',4'-Dibenzyloxy-7-(2-hydroxy-3-iso-propylamino-propoxy)-flavone (38);
f) 6-(3-tert-Butylamino-2-hydroxy-propoxy)-3',4'-dibenzyloxy-flavone (39);
g) 7-(3-tert-Butylamino-2-hydroxy-propoxy)-3',4',5'-trimethoxy-flavone (40);
h) 7-(2-Hydroxy-3-iso-propylamino-propoxy)-3',4',5'-trimethoxy-flavone (41);
i) 7-[2-Hydroxy-3-(4-phenylpiperazin-1-yl)-propoxy]-3',4',5'-trimethoxy-flavone (42);
j) 7-[3-tert-Butylamino-2-hydroxy-propoxy]-3',5'-dimethoxy flavone (43);
k) 3',5'-Dimethoxy-7-[2-hydroxy-3-iso-propylamino-propoxy]-flavone (44);
l) 3',5'-Dimethoxy-7-[2-hydroxy-3-(4-phenylpiperazin-1-yl)-propoxy]-flavone (45);
m) 3',4'-Dimethoxy-7-[2-hydroxy-3-iso-propylamino-propoxy]-flavone (46);
n) 3',4'-Dimethoxy-7-[2-hydroxy-3-(4-phenylpiperazin-1-yl)-propoxy]-flavone (47);
o) 7-(3-tert-Butylamino-2-hydroxy-propoxy)-3',5'-dihydroxy-flavone (48);
p) 3',5'-Dihydroxy-7-(2-hydroxy-3-iso-propylamino-propoxy)-flavone (49);
q) 7-(3-tert-Butylamino-2-hydroxy-propoxy)-3',4'-dihydroxy-flavone (50);
r) 3',4'-Dihydroxy-7-(2-hydroxy-3-iso-propylamino-propoxy)-flavone (51);
s) 6-(3-tert-Butylamino-2-hydroxy-propoxy)-3',4'-dihydroxy-flavone (52).

Yet another embodiment of the present invention provides a compound having formula I or a pharmaceutically acceptable salt thereof, wherein the representative compounds are:
a) 3',5'-Dibenzyloxy-7-{2-[4-(thiazolidin-2,4-dione-5-ylidinemethyl)-phenoxy]-ethoxy}-flavone (62);
b) 3',4'-Dibenzyloxy-7-{2-[4-(thiazolidin-2,4-dione-5-ylidinemethyl)-phenoxy]-ethoxy}-flavone (63);
c) 7-{2-[4-(thiazolidin-2,4-dione-5-ylidinemethyl)-phenoxy]-ethoxy}-3',4',5'-trimethoxy-flavone (64);
d) 7-{3-[4-(thiazolidin-2,4-dione-5-ylidinemethyl)-phenoxy]-propoxy}-3',4',5'-trimethoxy-flavone (65);
e) 3',5'-Dimethoxy-7-{3-[4-(thiazolidin-2,4-dione-5-ylidinemethyl)-phenoxy]-propoxy}-flavone (66);
f) 3',4'-Dimethoxy-7-{3-[4-(thiazolidin-2,4-dione-5-ylidinemethyl)-phenoxy]-propoxy}-flavone (67).

Synthesis of Substituted Ethyl Benzoates

All the required substituted ethyl benzoates for the synthesis of flavones were prepared using the standard procedure as described in Vogel's textbook of practical organic chemistry (Vogel, A. I.; "Text Book Of Practical Organic chemistry" 5$^{th}$ edition, Revised by Furnish, B. S.; Hannaford, A. J.; Smith, P. W. G.; Tatchell, A. R. pp: 1077 [esterification], 1139 [Benzylation]). Esterification of appropriately substituted benzoic acid (1-2, 10-12) was achieved by refluxing it in dry ethanol with catalytic amount of concentrated sulphuric acid. The dihydroxy ethyl benzoate (3-4) was benzylated with benzyl bromide in presence of potassium carbonate in acetone at room temperature (Scheme 1&2). Methylation followed by esterification of 3,4-dimethoxy benzoic acid (13) was carried out with dimethyl sulphate and aqueous sodium hydroxide in ethanol. The unesterified 3,4-dimethoxy benzoic acid (10) was further esterified to 7 as described above (Scheme 3).

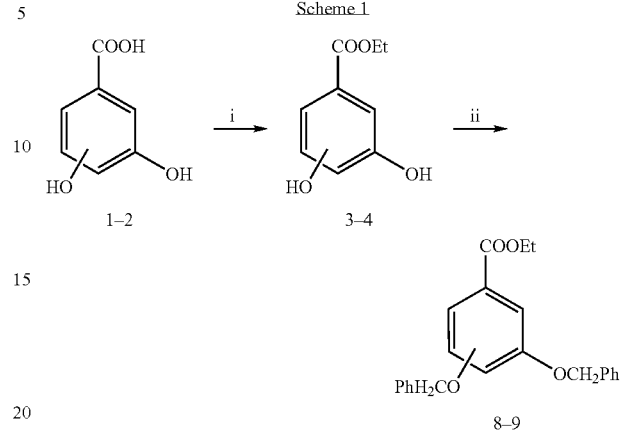

Reagents and Conditions: (i). Ethanol, H$_2$SO$_4$, Reflux (ii). Benzyl bromide, K$_2$CO$_3$, Acetone, RT.

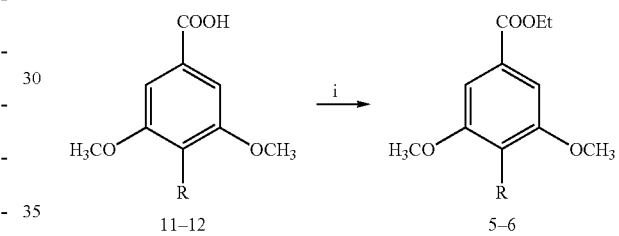

Reagents and Conditions: (i). Ethanol, H$_2$SO$_4$, Reflux.

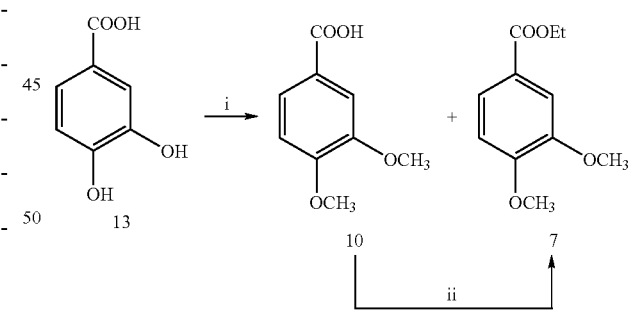

Reagents and Conditions: (i). DMS, Aq. NaOH, Ethanol, Reflux (ii). Ethanol, H$_2$SO$_4$, Reflux.

Synthesis of Flavone Derived Propanolamines

Flavone derived propanolamines were synthesized as shown in Scheme 4 and presented in Table 1. Firstly, flavones were synthesized using the reported procedure with slight modifications (Cushman, M.; Nagarathnam, D. *Tet. Lett.* 1990, 31, 6497). We used ethyl benzoates and Dowex-H$^+$ in 2-propanol in place of benzoyl chlorides and acetic acid-sulphuric acid respectively. Reaction of dihydroxy acetophenone (14-15) with substituted ethyl benzoate (5-9) in the presence of lithiumhexamethyldisilazane (LIHMDS) in dry tetrahydrofuran furnished the corresponding substituted 1,3-dibenzoyl methanes (16-21). Cyclization of 16-21 with Dowex-H⁺ in 2-propanol at reflux yielded the respective flavones (22-27). The substituted hydroxy flavone (22-27) was then allowed to react with epichlorohydrin in the presence of sodium hydride in dry dimethyl formamide to yield 2,3-epoxy-propoxy-flavones (28-33). The purified epoxide (28-33) was heated under reflux with amines in methanol to yield propanolamines (34-47). The dibenzylated flavone derived propanolamine (34-39) was further debenzylated under catalytic hydrogenation process to yield the corresponding dihydroxy flavone derived propanolamines (48-52).

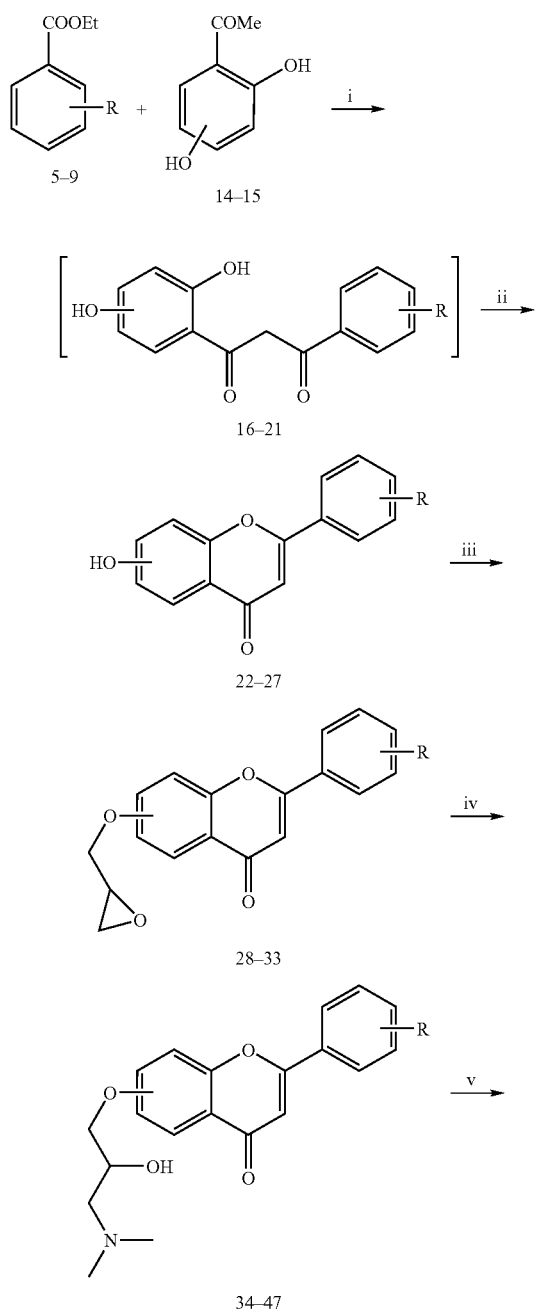

Scheme 4

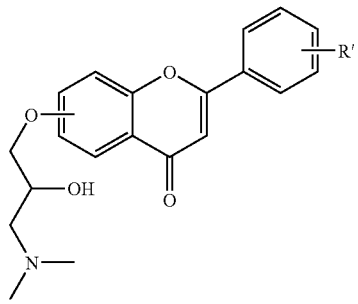

48–52

Reagents and Conditions: (i). LIHMDS, THF, -70° C. (ii). Dowex-H⁺, 2-Propanol, Reflux (iii). Epichlorohydrin, NaH, DMF, RT (vi). Amine, Methanol, Reflux (v). H₂—Pd/C, Methanol.

Synthesis of 4-(Thiazolidin-2,4-dione-5-ylidinemethyl)-Phenol 4-(Thiazolidin-2,4-dione-5-ylidinemethyl)-phenol (55) was synthesized by the condensation of 4-hydroxy benzaldehyde (53) with commercially available 2,4-thiazolidinedione (54) using piperidine as base in refluxing ethanol, according to a known procedure (Momose, Y.; Meguro, K.; Ikeda, H.; Hatanaka, C.; Oi, S.; Sohda, T. *Chem. Pharm. Bull.* 1991, 39, 1440.) (Scheme 5).

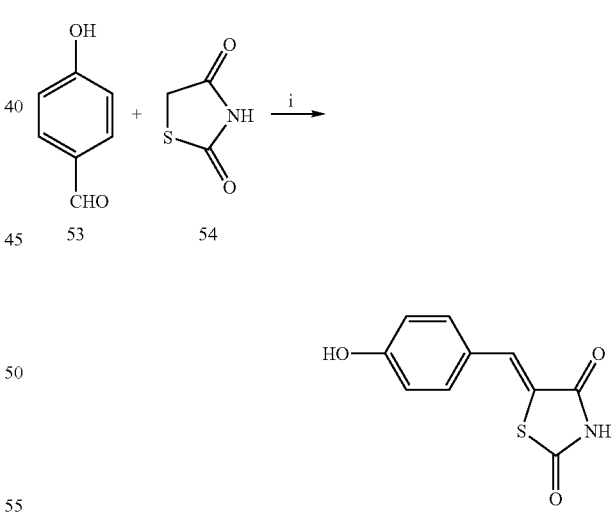

Scheme 5

Reagents and Conditions: (i). Ethanol, Piperidine, Reflux.

Synthesis of Flavone Derived Thiazolidinediones

Bromo alkoxy flavones (56-61) were prepared by the reaction of flavone (22-27) with dibromo alkane. Reaction of 55 with dibromo alkoxy flavone in dry dimethyl formamide provided the target compounds (62-67). (Scheme 6 and Table 2).

Scheme 6

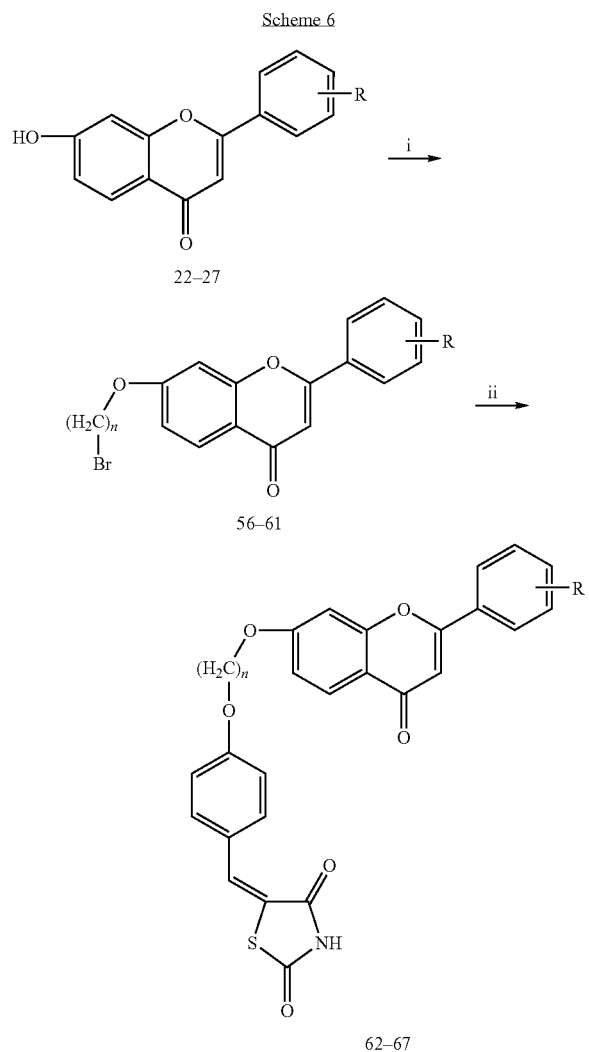

Reagents and Conditions: (i). Dibromo alkane, $K_2CO_3$, DMF, RT (ii). 55, $K_2CO_3$, DMF, RT.

TABLE 1

| Compd. No. | Position | $R_4, R_5, R_6$ | Amine | Formula |
|---|---|---|---|---|
| 34 | 7 | 3',5'-dibenzyloxy | t-butyl | $C_{36}H_{37}NO_6$ |
| 35 | 7 | 3',5'-dibenzyloxy | i-propyl | $C_{35}H_{35}NO_6$ |
| 36 | 7 | 3',5'-dibenzyloxy | 4-phenyl piperazine-1-yl | $C_{42}H_{40}N_2O_6$ |
| 37 | 7 | 3',4'-dibenzyloxy | t-butyl | $C_{36}H_{37}NO_6$ |
| 38 | 7 | 3',4'-dibenzyloxy | i-propyl | $C_{35}H_{35}NO_6$ |
| 39 | 6 | 3',4'-dibenzyloxy | t-butyl | $C_{36}H_{37}NO_6$ |
| 40 | 7 | 3',4',5'-trimethoxy | t-butyl | $C_{25}H_{31}NO_7$ |
| 41 | 7 | 3',4',5'-trimethoxy | i-propyl | $C_{24}H_{29}NO_7$ |
| 42 | 7 | 3',4',5'-trimethoxy | 4-phenyl piperazine-1-yl | $C_{31}H_{34}N_2O_7$ |
| 43 | 7 | 3',5'-dimethoxy | t-butyl | $C_{24}H_{29}NO_6$ |
| 44 | 7 | 3',5'-dimethoxy | i-propyl | $C_{23}H_{27}NO_6$ |
| 45 | 7 | 3',5'-dimethoxy | 4-phenyl piperazine-1-yl | $C_{30}H_{32}N_2O_6$ |
| 46 | 7 | 3',4'-dimethoxy | i-propyl | $C_{23}H_{27}NO_6$ |
| 47 | 7 | 3',4'-dimethoxy | 4-phenyl piperazine-1-yl | $C_{30}H_{32}N_2O_6$ |
| 48 | 7 | 3',5'-dihydroxy | t-butyl | $C_{22}H_{25}NO_6$ |
| 49 | 7 | 3',5'-dihydroxy | i-propyl | $C_{21}H_{23}NO_6$ |
| 50 | 7 | 3',4'-dihydroxy | t-butyl | $C_{22}H_{25}NO_6$ |
| 51 | 7 | 3',4'-dihydroxy | i-propyl | $C_{21}H_{23}NO_6$ |
| 52 | 6 | 3',4'-dihydroxy | t-butyl | $C_{22}H_{25}NO_6$ |

TABLE 2

| Compd. No. | n | $R_4, R_5, R_6$ | Formula |
|---|---|---|---|
| 62 | 2 | 3',5'-dibenzyloxy | $C_{41}H_{31}NO_8S$ |
| 63 | 2 | 3',4'-dibenzyloxy | $C_{41}H_{31}NO_8S$ |
| 64 | 2 | 3',4',5'-trimethoxy | $C_{30}H_{25}NO_9S$ |
| 65 | 3 | 3',4',5'-trimethoxy | $C_{31}H_{27}NO_9S$ |
| 66 | 3 | 3',5'-dimethoxy | $C_{30}H_{25}NO_8S$ |
| 67 | 3 | 3',4'-dimethoxy | $C_{30}H_{25}NO_8S$ |

The invention is further elaborated with the help of following examples. However, these examples should not be construed to limit the scope of the invention.

EXAMPLES

Ethyl-3,5-dihydroxy-benzoate (3)

To a solution of 3,5-dihydroxy benzoic acid, 1 (19 g, 123 mmol) in dry ethanol (250 mL) was added 2-3 mL of concentrated sulphuric acid drop wise and refluxed for 8 h. Ethanol was evaporated on rotavapor, diluted with water and extracted with ether. Combined ethereal layers were again washed with saturated sodium bicarbonate solution, water and dried over sodium sulphate, filtered and evaporated to dryness to afford 3. Yield 16.8 g (75%); mp 128-130° C.; MS (FAB) 183 ($M^+$+1); IR (KBr) 3496, 1819, 1687; $^1$H NMR (200 MHz, DMSO-$d_6$) δ 9.89 (s, 2H), 7.06 (d, J=2.2 Hz, 2H), 6.69 (t, J=2.2 Hz, 1H), 4.48 (q, J=7.1 Hz, 2H), 1.52 (t, J=7.1 Hz, 3H).

Ethyl-3,4-dihydroxy-benzoate (4)

Esterification of 3,4-dihydroxy benzoic acid, 2 (30.8 g, 200 mmol) was carried out using the same method as described for 3 to afford 4. Yield 29.7 g (82%); mp 133-134° C.; MS (FAB) 183 ($M^+$+1); IR (KBr) 3498, 3471, 1819, 1685; $^1$H NMR (200 MHz, DMSO-$d_6$) δ 7.20 (d, J=1.9 Hz, 1H), 7.15 (dd, J=8.2 Hz, 2.0 Hz, 1H), 6.65 (d, J=8.2 Hz, 1H), 4.04 (q, J=7.1 Hz, 2H), 1.09 (t, J=7.1 Hz, 3H).

Ethyl-3,4,5-trimetboxy-benzoate (5)

Esterification of 3,4,5-trimethoxy benzoic acid, 11 (21.2 g, 100 mmol) was carried out using the same method as described for 3 to afford 5. Yield 17.9 g (75%); mp 56-57° C.; MS (FAB) 241 ($M^+$+1); IR (KBr) 1967, 1708; $^1$H NMR (200 MHz, CDCl$_3$) δ 7.30 (s, 2H), 4.38 (q, J=7.1 Hz, 2H), 3.91 (s, 9H), 1.40 (t, J=7.1 Hz, 3H).

Ethyl-3,5-dimethoxy-benzoate (6)

Esterification of 3,5-dimethoxy benzoic acid, 12 (8.8 g, 48 mmol) was carried out using the same method as described for 3 to afford 6. Yield 9.5 g (94%); mp Liquid at RT; MS (FAB) 211 ($M^+$+1); IR (KBr) 1970, 1716; $^1$H NMR (200 MHz, CDCl$_3$) δ 7.18 (d, J=2.3 Hz, 2H), 6.64 (d, J=2.3 Hz, 1H), 4.36 (q, J=7.1 Hz, 2H), 3.82 (s, 6H), 1.39 (t, J=7.1 Hz, 3H).

Ethyl-3,4-dimethoxy-benzoate(7)/benzoic acid (10)

Dimethyl sulphate (16.4 mL, 130 mmol) and 20% aqueous sodium hydroxide solution (in excess) were added drop wise to a solution of 3,4-dihydroxy benzoic acid, 13 (20 g, 130 mmol) in ethanol (250 mL) over a period of 3 h and further stirred at room temperature for 3 h. During this process esterification also took place because of the acid generated in situ from dimethyl sulphate. Ethanol was evaporated on rotavapor, diluted with water and extracted with ether. Combined ethereal layers were again washed with saturated sodium bicarbonate solution, dried over sodium sulphate, filtered and upon concentration afforded the required compound ethyl-3,4-dimethoxy-benzoate (7). 3,4-Dimethoxy benzoic acid (10) was liberated form aqueous layer by acidifying with dilute hydrochloric acid, which was further esterified to 7 in a similar manner as described for 3.

Ethyl-3,4-dimethoxy-benzoate (7). Yield 24.5 g (90%); mp Liquid at RT; MS (FAB) 211 (M$^+$+1); IR (KBr) 1974, 1712; $^1$H NMR (200 MHz, CDCl$_3$) δ 7.68 (d, J=8.4 Hz, 1H), 7.55 (s, 1H), 6.88 (d, J=8.4 Hz, 1H), 4.36 (q, J=7.1 Hz, 2H), 3.93 (s, 3H), 3.89 (s, 3H), 1.39 (t, J=7.1 Hz, 3H).

3,4-Dimethoxy-benzoic acid (10). Yield 2 g (8%); mp 179-181° C.; MS (FAB) 183 (M$^+$+1); IR (KBr) 2939, 2836, 1867, 1678; $^1$H NMR (200 MHz, CDCl$_3$) δ 7.79 (dd, J=8.4 Hz, 1.9 Hz, 1H), 7.60 (d, J=1.8 Hz, 1H), 6.93 (d, J=8.5 Hz, 1H), 3.96 (s, 6H).

Ethyl-3,5-dibenzyloxy-benzoate (8)

To a solution of ethyl-3,5-dihydroxy benzoate, 3 (16.8 g, 92 mmol) in acetone (350 mL) were added potassium carbonate (27.6 g, 200 mmol) and benzyl bromide (23.8 mL, 200 mmol) and stirred at room temperature for 9 h. Reaction mixture was filtered, concentrated on rotavapor and the crude product purified by column chromatography to afford 8. Yield 24.7 g (74%); mp 63-65° C.; MS (FAB) 363 (M$^+$+1); IR (KBr) 1824, 1708; $^1$H NMR (200 MHz, CDCl$_3$) δ 7.34-7.35 (m, 10H), 7.30 (d, J=2.3 Hz, 2H), 6.79 (t, J=2.2 Hz, 1H), 5.07 (s, 4H), 4.36 (q, J=7.1 Hz, 2H), 1.38 (t, J=7.1 Hz, 3H).

Ethyl-3,4-dibenzyloxy-benzoate (9)

Ethyl-3,4-dihydroxy benzoate, 4 (27.3 g, 150 mmol), benzyl bromide (40.4 mL, 340 mmol) and potassium carbonate (41.4 g, 300 mmol) in acetone (350 mL) were reacted in a similar manner as described for 8 to afford 9. Yield 41.4 g (76%); mp 68-69° C.; MS (FAB) 363 (M$^+$+1); IR (KBr) 1889, 1707; $^1$H NMR (200 MHz, CDCl$_3$) δ 7.65 (s, 1H), 7.63 (dd, J=8.7 Hz, 1.7 Hz, 1H), 7.48-7.25 (m, 10H), 6.91 (d, J=8.3 Hz, 1H), 5.19 (s, 2H), 5.18 (s, 2H), 4.31 (q, J=7.1 Hz, 2H), 1.35 (t, J=7.1 Hz, 3H).

3',5'-Dibenzyloxy-7-hydroxy-flavone (22)

A solution of 20% lithiumhexamethyldisilazane in tetrahydrofuran (217.5 mL, 260 mmol) was added to a well-stirred solution of 2,4-dihydroxy acetophenone, 14 (9.88 g, 65 mmol) in tetrahydrofuran (150 mL) under nitrogen atmosphere at −78° C. for 30 min. The reaction mixture was stirred at −78° C. for 1 h and at −30° C. for 2 h. It was again cooled to −78° C. and a solution of ethyl-3,5-dibenzyloxy-benzoate 8 (23.5 g, 65 mmol) in tetrahydrofuran (100 mL) was added over a period of 30 min. It was further stirred at room temperature for overnight and poured into ice water containing hydrochloric acid. It was extracted with chloroform, dried over sodium sulphate, filtered and evaporated on rotavapor to afford 1-(3,5-bis-benzyloxy-phenyl)-3-(2,4-dihydroxy-phenyl)-propane-1,3-dione (16). The residue, 16 (37.8 g) was refluxed with Dowex-H$^+$ (8 g) in 2-propanol (300 mL) for 3-4 h. 2-Propanol was evaporated on rotavapor, residue suspended in hot dimethyl formamide and filtered. The filtrate was concentrated under reduced pressure and the product was washed with cooled methanol (3*200 mL) to afford 22. Yield 23.8 g (81%); mp 248-249° C.; MS (FAB) 451 (M$^+$+1); IR (KBr) 3452, 1620; $^1$H NMR (200 MHz, DMSO-d$_6$) δ 7.84 (d, J=8.7 Hz, 1H), 7.52-7.28 (m, 10H), 7.23 (d, J=1.9 Hz, 2H), 6.98 (d, J=2.0 Hz, 1H), 6.89 (s, 1H), 6.89 (dd, J=8.6 Hz, 2.1 Hz, 1H), 6.82 (s, 1H), 5.14 (s, 4H).

3',4'-Dibenzyloxy-7-hydroxy-flavone (23)

A solution of 20% lithiumhexamethyldisilazane in tetrahydrofuran (200.8 mL, 240 mmol), 2,4-dihydroxy acetophenone, 14 (9.12 g, 60 mmol) in tetrahydrofuran (150 mL) and ethyl-3,4-dibenzyloxy benzoate, 9 (21.7 g, 60 mmol) in tetrahydrofuran (100 mL) were reacted to afford 17, 1-(3,4-bisbenzyloxy-phenyl)-3-(2,4-dihydroxy-phenyl)-propane-1,3-dione (55 g), which was then cyclized with Dowex-H$^+$ (12 g) in 2-propanol (400 mL) in a similar way as described for 22 to afford 23 (Frederique, A. A. A.; Hageman, J. A.; Guido, R. M. M. H.; Van Der Vijgh, W. J. F.; Bast, A.; Menge, W. M. P. B. *J. Med. Chem.* 2000, 43, 3752.). Yield 24 g (89%); mp 245-247° C. (lit. 244-245° C.); MS (FAB) 451 (M$^+$+1); IR (KBr) 3426, 1607; $^1$H NMR (200 MHz, DMSO-d$_6$) δ 10.79 (s, 1H), 7.86 (d, J=8.6 Hz, 1H), 7.68 (s, 1H), 7.60 (d, J=8.8 Hz, 1H), 7.51-7.30 (m, 10H), 7.18 (d, J=8.5 Hz, 1H), 6.98 (s, 1H), 6.91 (d, J=8.8 Hz, 1H), 6.83 (s, 1H), 5.26 (s, 2H), 5.21 (s, 2H).

3',4'-Dibenzyloxy-6-hydroxy-flavone (24)

A solution of 20% lithiumhexamethyldisilazane in tetrahydrofuran (200.8 mL, 240 mmol), 2,5-dihydroxy acetophenone, 15 (9.12 g, 60 mmol) in tetrahydrofuran (150 mL) and ethyl-3,4-dibenzyloxy benzoate, 9 (21.7 g, 60 mmol) in tetrahydrofuran (100 mL) were reacted to afford 18, 1-(3,4-bisbenzyloxy-phenyl)-3-(2,5-dihydroxy-phenyl)-propane-1,3-dione (41 g), which was cyclized with Dowex-H+(12 g) in 2-propanol (300 mL) in a similar way as described for 22 to afford 24. Yield 12 g (44%); mp 196-197° C.; MS (FAB) 451 (M$^+$+1); IR (KBr) 3419, 1621; $^1$H NMR (200 MHz, DMSO-d$_6$) δ 10.08 (s, 1H), 7.75 (s, 1H), 7.69 (d, J=8.7 Hz, 1H), 7.63 (s, 1H), 7.55-7.22 (m, 13H), 6.94 (s, 1H), 5.30 (s, 2H), 5.27 (s, 2H).

7-Hydroxy-3',4',5'-trimethoxy-flavone (25)

A solution of 20% lithiumhexamethyldisilazane in tetrahydrofuran (335 mL, 400 mmol), 2,4-dihydroxy acetophenone, 14 (15.2 g, 100 mmol) in tetrahydrofuran (150 mL) and ethyl-3,4,5-trimethoxy benzoate, 5 (24 g, 100 mmol) in tetrahydrofuran (100 mL) were reacted to afford 19, 1-(3,4,5-trimethoxy-phenyl)-3-(2,4-dihydroxy-phenyl)-propane-1,3-dione (37 g), which was cyclized with Dowex-H$^+$ (14 g) in 2-propanol (500 mL) in a similar way as described for 22 to afford 25 (Gaydou, E. M.; Bianchi, J. P. *Bull. Soc. Chim. Fr.* 1978, II-43.). Yield 27 g (82%); mp 284-286° C. (lit. 279-280° C.); MS (FAB) 329 (M$^+$+1); IR (KBr) 3408, 1630; $^1$H NMR (200 MHz, DMSO-d$_6$) δ 7.86 (d, J=8.7 Hz, 1H), 7.29 (s, 2H), 7.03 (d, J=1.8 Hz, 1H), 6.96 (s, 1H), 6.92 (d, J=8.9 Hz, 1H), 3.89 (s, 6H), 3.79 (s, 3H).

3',5'-Dimethoxy-7-hydroxy-flavone (26)

A solution of 20% lithiumhexamethyldisilazane in tetrahydrofuran (144 mL, 172 mmol), 2,4-dihydroxy acetophenone, 14 (6.5 g, 43 mmol) in tetrahydrofuran (150 mL) and ethyl-3,5-dimethoxy benzoate, 6 (9 g, 43 mmol) in tetrahydrofuran (100 mL) were reacted to afford 20, 1-(3,5-dimethoxy-phenyl)-3-(2,4-dihydroxy-phenyl)-propane-1,3-dione (15 g), which was cyclized with Dowex-H$^+$ (5 g) in 2-propanol (200 mL) in a similar way as described for 22 to afford 26. Yield 7.6 g (59%); mp 267-268° C.; MS (FAB) 299 (M$^+$+1); IR (KBr) 3405, 1602; $^1$H NMR (200 MHz, DMSO-d$_6$) δ 10.82 (s, 1H), 7.89 (d, J=8.7 Hz, 1H), 7.17 (d, J=2.0 Hz, 2H), 7.03 (d, J=1.9 Hz, 1H), 6.95 (s, 1H), 6.94 (dd, J=7.2 Hz, 2.0 Hz, 1H), 6.71 (s, 1H), 3.85 (s, 6H).

3',4'-Dimethoxy-7-hydroxy-flavone (27)

A solution of 20% lithiumhexamethyldisilazane in tetrahydrofuran (335 mL, 400 mmol), 2,4-dihydroxy acetophenone, 14 (15.2 g, 100 mmol) in tetrahydrofuran (150 mL) and ethyl-3,4-dimethoxy benzoate, 7 (21 g, 100 mmol) in tetrahydrofuran (100 mL) were reacted to afford 21, 1-(3,4-dimethoxy-phenyl)-3-(2,4-dihydroxy-phenyl)-propane-1,3-dione (37 g), which was cyclized with Dowex-H$^+$ (15 g) in 2-propanol (250 mL) in a similar way as described for 22 to afford 27. Yield 15.4 g, (52%); mp 263-265° C.; MS (FAB) 299 (M$^+$+1); IR (KBr) 3452, 1625; $^1$H NMR (200 MHz, CDCl$_3$+DMSO-d$_6$) δ 9.83 (s, 1H), 7.32 (d, J=8.5 Hz, 1H), 6.97 (dd, J=8.5 Hz, 1.7 Hz, 1H), 6.83 (d, J=1.7 Hz, 1H), 6.43 (d, J=8.5 Hz, 1H), 6.34 (s, 1H), 6.30 (dd, J=9.7 Hz, 2.0 Hz, 1H), 6.08 (s, 1H), 3.35 (s, 3H), 3.32 (s, 3H).

3',5'-Dibenzyloxy-7-(2,3-epoxy-propoxy)-flavone (28)

To a well-stirred solution of 3',5'-dibenzyloxy-7-hydroxy-flavone, 22 (8 g, 17.8 mmol) in dry dimethyl formamide (200 mL) was added 50% sodium hydride (3 g, 125 mmol) at 0-5° C. and after 30 minutes, excess of epichlorohydrin (8.3 mL, 107 mmol) was added and stirred at room temperature for overnight. The reaction mixture was concentrated under reduced pressure, diluted with water and extracted with chloroform. The combined organic layers were dried over sodium sulphate, filtered and evaporated to dryness. The crude product was purified by column chromatography to afford 28. Yield 7.1 g (79%); mp 172-173° C.; MS (FAB) 507 (M$^+$+1); IR (KBr) 1640; $^1$H NMR (200 MHz, CDCl$_3$) δ 8.13 (d, J=8.7 Hz, 1H), 7.47-7.34 (m, 10H), 7.11 (d, J=2.2 Hz, 2H), 7.00 (dd, J=10.9 Hz, 2.1 Hz, 1H), 6.97 (d, J=1.9 Hz, 1H), 6.77 (d, J=2.0 Hz, 1H), 6.69 (s, 3H), 5.10 (s, 4H), 4.38 (dd, J=11.1 Hz, 2.8 Hz, 1H), 4.04 (dd, J=11.1 Hz, 5.8 Hz, 1H), 3.41-3.40 (m, 1H), 2.95 (t, J=4.5 Hz, 4.5 Hz, 1H), 2.80 (dd, J=4.8 Hz, 2.6 Hz, 1H); $^{13}$C NMR δ 177.9, 163.8, 162.9, 160.7, 158.1, 136.7, 133.9, 129.1, 128.6, 127.9, 127.5, 118.2, 115.1, 108.1, 106.0, 105.4, 101.7, 70.8, 69.7, 50.2, 44.9.

3',4'-Dibenzyloxy-7-(2,3-epoxy-propoxy)-flavone (29)

Reaction of 3',4'-dibenzyloxy-7-hydroxy-flavone, 23 (10 g, 22.2 mmol), 50% sodium hydride (3 g, 125 mmol) and epichlorohydrin (6.9 mL, 88 mmol) in dry dimethyl formamide (160 mL) using identical procedure as described for 28 furnished 29. Yield 9.7 g (86%); mp 168-170° C.; MS (FAB) 507 (M$^+$+1); IR (KBr) 1639; $^1$H NMR (200 MHz, CDCl$_3$) δ 8.12 (d, J=8.7 Hz, 1H), 7.50-7.32 (m, 12H), 7.04-6.93 (m, 3H), 6.61 (s, 1H), 5.24 (s, 4H), 4.38 (dd, J=11.1 Hz, 2.9 Hz, 1H), 4.05 (dd, J=11.1 Hz, 5.8 Hz, 1H), 3.42-3.40 (m, 1H), 2.96 (t, J=4.5 Hz, 4.5 Hz, 1H), 2.80 (dd, J=4.8 Hz, 2.6 Hz, 1H).

3',4'-Dibenzyloxy-6-(2,3-epoxy-propoxy)-flavone (30)

Reaction of 3',4'-dibenzyloxy-6-hydroxy-flavone, 24 (4.5 g, 10 mmol), 50% sodium hydride (1.4 g, 60 mmol) and epichlorohydrin (4.7 mL, 60 mmol) in dry dimethyl formamide (120 mL) using identical procedure as described for 28 furnished 30. Yield 4.2 g (81%); mp 147-149° C.; MS (FAB) 507 (M$^+$+1); IR (KBr) 1610; $^1$H NMR (200 MHz, CDCl$_3$) δ 7.57-7.29 (m, 15H), 7.02 (d, J=8.6 Hz, 1H), 6.66 (s, 1H), 5.25 (s, 4H), 4.39 (dd, J=11.0 Hz, 2.6 Hz, 11H), 3.98 (dd, J=11.0 Hz, 6.0 Hz, 1H), 3.40-3.39 (m, 1H), 2.93 (t, J=4.5 Hz, 4.5 Hz 1H), 2.78 (dd, J=4.8 Hz, 2.6 Hz, 1H).

7-(2,3-Epoxy-propoxy)-3',4',5'-trimethoxy-flavone (31)

Reaction of 3',4',5'-trimethoxy-7-hydroxy-flavone, 25 (8.2 g, 25 mol), 50% sodium hydride (3 g, 125 mmol) and epichlorohydrin (7.8 mL, 100 mmol) in dry dimethyl formamide (145 mL) using identical procedure as described for 28 furnished 31. Yield 8 g (83%); mp 187-188° C.; MS (FAB) 385 (M$^+$+1); IR (KBr) 1651; $^1$H NMR (200 MHz, CDCl$_3$) δ 8.14 (d, J=9.3 Hz, 1H), 7.10 (s, 2H), 7.02 (d, J=7.6 Hz, 1H), 7.00 (s, 1H), 6.70 (s, 1H), 4.39 (dd, J=11.0 Hz, 2.8 Hz, 1H), 3.98 (dd, J=11.0 Hz, 5.7 Hz, 1H), 3.43-3.39 (m, 1H), 3.96 (s, 6H), 3.93 (s, 3H), 2.97 (t, J=4.5 Hz, 4.2 Hz, 1H), 2.82 (dd, J=4.7 Hz, 2.2 Hz, 1H).

3',5'-Dimethoxy-7-(2,3-epoxy-propoxy)-flavone (32)

Reaction of 3',5'-dimethoxy-7-hydroxy-flavone, 26 (2 g, 6.7 mol), 50% sodium hydride (0.96 g, 40 mmol) and epichlorohydrin (1.6 mL, 20 mmol) in dry dimethyl formamide (90 mL) using identical procedure as described for 28 furnished 32. Yield 1.7 g (72%); mp 181-182° C.; MS (FAB) 355 (M$^+$+1); IR (KBr) 1630; $^1$H NMR (200 MHz, CDCl$_3$) δ 8.14 (dd, J=8.3 Hz, 0.77 Hz, 1H), 7.04-6.99 (m, 4H), 6.73 (s, 1H), 6.61 (t of dd, J=2.2 Hz, 2.2 Hz, 2.2 Hz, 1H), 4.39 (dd, J=11.1 Hz, 2.9 Hz, 1H), 4.06 (dd, J=11.1 Hz, 5.8 Hz, 1H), 3.87 (s, 6H), 3.44-3.39 (m, 1H), 2.96 (t, J=4.5 Hz, 4.5 Hz, 1H), 2.80 (dd, J=4.8 Hz, 2.6 Hz, 1H).

3',4'-Dimethoxy-7-(2,3-epoxy-propoxy)-flavone (33)

Reaction of 3',4'-dimethoxy-7-hydroxy-flavone, 27 (6 g, 20 mol), 50% sodium hydride (2.4 g, 100 mmol) and epichlorohydrin (3.9 mL, 50 mmol) in dry dimethyl formamide (200 mL) using identical procedure as described for 28 furnished 33. Yield 5.3 g (74%); mp 148-149° C.; MS (FAB) 355 (M$^+$+1); IR (KBr) 1632; $^1$H NMR (200 MHz, CDCl$_3$) δ 8.13 (d, J=9.5 Hz, 1H), 7.73 (dd, J=8.5 Hz, 2.0 Hz, 1H), 7.35 (d, J=1.9 Hz, 1H), 7.00 (dd, J=7.1 Hz, 2.3 Hz, 1H), 6.99 (d, J=2.2 Hz, 1H), 6.97 (d, J=8.5 Hz, 1H), 6.68 (s, 1H), 4.39 (dd, J=11.1 Hz, 2.9 Hz, 1H), 4.05 (dd, J=11.1 Hz, 5.8 Hz, 1H), 3.98 (s, 3H), 3.96 (s, 3H), 3.44-3.40 (m, 1H), 2.96 (t, J=4.5 Hz, 4.5 Hz, 1H), 2.81 (dd, J=4.8 Hz, 2.6 Hz, 1H).

7-(3-tert-Butylamino-2-hydroxy-propoxy)-3',5'-dibenzyloxy-flavone (34)

A solution of 3',5'-dibenzyloxy-7-(2,3-epoxy-propoxy)-flavone, 28 (2.5 g, 4.9 mmol) and tert-butyl amine (1.05 mL, 9.8 mmol) in dry methanol (150 mL) was stirred at reflux for 6 h. Reaction mixture was concentrated on rotavapor and crude product purified by column chromatography to afford 34. Yield 2.6 g (93%); mp 170-171° C.; MS (FAB) 580 (M$^+$+1); IR (KBr) 3428, 1648; $^1$H NMR (200 MHz, CDCl$_3$) δ 8.02 (d, J=8.8 Hz, 1H), 7.59-7.33 (m, 10H), 7.13 (d, J=1.9 Hz, 2H), 7.07 (s, 1H), 7.01 (dd, J=9.8 Hz, 2.0 Hz, 1H), 6.76 (s, 1H), 6.71 (s, 1H), 5.12 (s, 4H), 4.57-4.54 (m, 1H), 4.27-4.16 (m, 2H), 3.24 (d, J=10.5 Hz, 1H), 3.05 (t, J=10.6 Hz, 1H), 1.45 (s, 9H); $^{13}$C NMR δ 178.3, 163.5, 163.2, 160.7, 158.1, 136.8, 133.9, 129.0, 128.6, 127.9, 127.5, 118.3, 115.2, 108.0, 105.9, 101.5, 72.9, 70.8, 67.5, 54.0, 45.3, 28.1. Analysis Calcd for C$_{36}$H$_{37}$NO$_6$: C, 74.59; H, 6.43; N, 2.42. Found: C, 74.44; H, 6.35; N, 2.51.

3',5'-Dibenzyloxy-7-(2-hydroxy-3-iso-propylamino-propoxy)-flavone (35).

3',5'-Dibenzyloxy-7-(2,3-epoxy-propoxy)-flavone, 28 (2.5 g, 4.9 mmol) and iso-propyl amine (1.8 mL, 14.7 mmol) in dry methanol (150 mL) were reacted in a similar manner to that described under 34 to afford 35. Yield 2.2 g (79%); mp 173-174° C.; MS (FAB) 566 (M$^+$+1); IR (KBr) 3431, 1637; $^1$H NMR (200 MHz, CDCl$_3$) δ 8.05 (d, J=8.6 Hz, 1H), 7.59-7.34 (m, 10H), 7.15 (d, J=1.8 Hz, 2H), 7.06 (s, 1H), 7.03 (d, J=9.4 Hz, 1H), 6.78 (s, 1H), 6.71 (s, 1H), 5.13 (s, 4H), 4.14-4.11 (m, 3H), 3.18-3.16 (m, 1H), 2.93-2.79 (m, 2H), 1.11 (d, J=6.2 Hz, 6H); $^{13}$C NMR δ 177.9, 163.8, 162.9, 160.6, 158.1, 136.7, 133.9, 128.9, 128.5, 127.8, 127.1, 118.1, 115.3, 108.0, 105.8, 105.3, 101.5, 71.7, 70.7, 68.4, 49.8, 49.3, 23.1, 23.0. Analysis Calcd for C$_{35}$H$_{35}$NO$_6$: C, 74.32; H, 6.24; N, 2.48. Found: C, 74.16; H, 6.17; N, 2.29.

3',5'-Dibenzyloxy-7-[2-hydroxy-3-(4-phenylpiperazin-1-yl)-propoxy]-flavone (36)

3',5'-Dibenzyloxy-7-(2,3-epoxy-propoxy)-flavone, 28 (2.5 g, 4.9 mmol) and 1-phenyl piperazine (0.76 mL, 5 mmol) in dry methanol (180 mL) were reacted in a similar manner to that described under 34 to afford 36. Yield 3.1 g (94%); mp 168-170° C.; MS (FAB) 669 (M$^+$+1); IR (KBr) 3389, 1634; $^1$H NMR (200 MHz, CDCl$_3$) δ 8.12 (d, J=8.6 Hz, 1H), 7.46-7.30 (m, 10H), 7.26-7.23 (m, 2H), 7.11 (d, J=1.9 Hz, 2H), 7.00 (d, J=8.5 Hz, 1H), 6.98 (s, 1H), 6.95-6.86 (m, 3H), 6.76 (s, 1H), 6.69 (s, 1H), 5.09 (s, 4H), 4.21-4.14 (m, 3H), 3.23 (t, J=4.7 Hz, 4.6 Hz, 4H), 2.91-2.81 (m, 2H), 2.66 (dd, J=5.2 Hz, 4.1 Hz, 4H). Analysis Calcd for C$_{42}$H$_{40}$N$_2$O$_6$: C, 75.43; H, 6.03; N, 4.19. Found: C, 75.37; H, 6.20; N, 4.13.

7-(3-tert-Butylamino-2-hydroxy-propoxy)-3',4'-dibenzyloxy-flavone (37)

3',4'-Dibenzyloxy-7-(2,3-epoxy-propoxy)-flavone, 29 (2.5 g, 4.9 mmol) and tert-butyl amine (1.05 mL, 9.8 mmol) in dry methanol (160 mL) were reacted in a similar manner to that described under 34 to afford 37. Yield 2.4 g (85%); mp 159-161° C.; MS (FAB) 580 (M+1); IR (KBr) 3400, 1633; $^1$H NMR (200 MHz, CDCl$_3$) δ 8.08 (d, J=8.7 Hz, 1H), 7.50-7.28 (m, 12H), 7.02-6.93 (m, 3H), 6.60 (s, 1H), 5.23 (s, 4H), 4.10-3.98 (m, 3H), 2.90 (dd, J=5.9 Hz, 3.8 Hz, 1H), 2.71 (dd, J=5.9 Hz, 7.3 Hz, 1H), 2.47 (s, 2H), 1.14 (s, 9H). Analysis Calcd for C$_{36}$H$_{37}$NO$_6$: C, 74.59; H, 6.43; N, 2.42 Found: C, 73.36; H, 6.62; N, 2.39.

3',4'-Dibenzyloxy-7-(2-hydroxy-3-iso-propylamino-propoxy)-flavone (38)

3',4'-Dibenzyloxy-7-(2,3-epoxy-propoxy)-flavone, 29 (2.5 g, 4.9 mmol) and iso-propyl amine (1.8 mL, 14.7 mmol) in dry methanol (160 mL) were reacted in a similar manner to that described under 34 to afford 38. Yield 2.4 g (87%); mp 177-179° C.; MS (FAB) 566 (M$^+$+1); IR (KBr) 3423, 1635; $^1$H NMR (200 MHz, CDCl$_3$) δ 8.02 (d, J=8.5 Hz, 1H), 7.70-7.32 (m, 12H), 7.11-6.98 (m, 3H), 6.64 (s, 1H), 5.24 (s, 2H), 5.23 (s, 2H), 4.14-4.09 (m, 3H), 3.05 (s, 2H), 2.92-2.68 (m, 3H), 1.09 (d, J=6.2 Hz, 6H). Analysis Calcd for C$_{35}$H$_{35}$NO$_6$: C, 74.32; H, 6.24; N, 2.48. Found: C, 74.46; H, 6.19; N, 2.36.

6-(3-tert-Butylamino-2-hydroxy-propoxy)-3',4'-dibenzyloxy-flavone (39)

3',4'-Dibenzyloxy-6-(2,3-epoxy-propoxy)-flavone, 30 (1.5 g, 3 mmol) and tert-butyl amine (0.96 mL, 9 mmol) in dry methanol (125 mL) were reacted in a similar manner to that described under 34 to afford 39. Yield 1.5 g (89%); mp 156-157° C.; MS (FAB) 580 (M$^+$+1); IR (KBr) 3404, 1621; $^1$H NMR (200 MHz, CDCl$_3$) δ 7.51-7.26 (m, 15H), 6.97 (d, J=8.9 Hz, 1H), 6.62 (s, 1H), 5.22 (s, 2H), 5.20 (s, 2H), 4.26-4.22 (m, 1H), 4.14-4.10 (m, 2H), 3.07-2.86 (m, 2H), 1.29 (s, 9H). Analysis Calcd for C$_{36}$H$_{37}$NO$_6$: C, 74.59; H, 6.43; N, 2.42. Found: C, 74.61; H, 6.62; N, 2.36.

7-(3-tert-Butylamino-2-hydroxy-propoxy)-3',4',5'-trimethoxy-flavone (40)

3',4',5'-Trimethoxy-7-(2,3-epoxy-propoxy)-flavone, 31 (2.1 g, 5.47 mmol) and tert-butyl amine (1.75 mL, 16.4 mmol) in dry methanol (130 mL) were reacted in a similar manner to that described under 34 to afford 40. Yield 2.1 g (84%); mp 119-120° C.; MS (FAB) 458 (M$^+$+1); IR (KBr) 3403, 1631; $^1$H NMR (200 MHz, CDCl$_3$) δ 8.11 (d, J=9.5 Hz, 1H), 7.10 (s, 2H), 7.02-6.99 (m, 2H), 6.70 (s, 1H), 4.14-4.11 (m, 3H), 3.96 (s, 6H), 3.93 (s, 3H), 2.86-2.81 (m, 2H), 1.14 (s, 9H). Analysis Calcd for C$_{25}$H$_{31}$NO$_7$: C, 65.63; H, 6.83; N, 3.06. Found: C, 65.47; H, 6.77; N, 3.12.

7-(2-Hydroxy-3-iso-propylamino-propoxy)-3',4',5'-trimethoxy-flavone (41)

3',4',5'-Trimethoxy-7-(2,3-epoxy-propoxy)-flavone, 31 (1.2 g, 3 mmol) and iso-propyl amine (0.78 mL, 9.3 mmol) in dry methanol (120 mL) were reacted in a similar manner to that described under 34 to afford 41. Yield 900 mg (65%); mp 106-107° C.; MS (FAB) 444 (M$^+$+1); IR (KBr) 3394, 1631; $^1$H NMR (200 MHz, CDCl$_3$) δ 8.09 (d, J=9.5 Hz, 1H), 7.10 (s, 2H), 7.10-6.99 (m, 2H), 6.71 (s, 1H), 4.16-4.09 (m, 3H), 3.96 (s, 6H), 3.93 (s, 3H), 2.95-2.82 (m, 3H), 1.14 (d, J=6.2 Hz, 6H).

Analysis Calcd for C$_{24}$H$_{29}$NO$_7$: C, 65.00; H, 6.59; N, 3.16. Found: C, 65.16; H, 6.47; N, 3.31.

7-[2-Hydroxy-3-(4-phenylpiperazin-1-yl)-propoxy]-3',4',5'-trimethoxy-flavone (42)

3',4',5'-Trimethoxy-7-(2,3-epoxy-propoxy)-flavone, 31 (1.1 g, 3 mmol) and 1-phenyl piperazine (0.5 mL, 3.27 mmol) in dry methanol (130 mL) were reacted in a similar manner to that described under 34 to afford 42. Yield 1.4 g (85%); mp 170-171° C.; MS (FAB) 547 (M$^+$+1); IR (KBr) 3406, 1635; $^1$H NMR (200 MHz, CDCl$_3$) δ 8.13 (d, J=9.5 Hz, 1H), 7.27 (t, J=7.9 Hz, 2H), 7.10 (s, 2H), 7.04-7.01 (m, 2H), 6.95-6.87 (m, 3H), 6.70 (s, 1H), 4.21-4.12 (m, 3H), 3.95 (s, 6H), 3.93 (s, 3H), 3.23 (t, J=4.6 Hz, 4H), 2.87-2.83 (m, 2H), 2.68-2.65 (m, 4H). Analysis Calcd for C$_{31}$H$_{34}$N$_2$O$_7$: C, 68.12; H, 6.27; N, 5.12. Found: C, 68.26; H, 6.37; N, 5.41.

7-[3-tert-Butylamino-2-hydroxy-propoxy]-3',5'-dimethoxy flavone (43)

3',5'-Dimethoxy-7-(2,3-epoxy-propoxy)-flavone, 32 (500 mg, 1.41 mmol) and tert-butyl amine (0.6 mL, 5.64 mmol) in dry methanol (100 mL) were reacted in a similar manner to that described under 34 to afford 43. Yield 400 mg (66%); mp 145-146° C.; MS (FAB) 428 (M+1); IR (KBr) 3431, 1631; $^1$H NMR (200 MHz, DMSO-d$_6$) δ 7.93 (d, J=8.8 Hz, 1H), 7.32 (d, J=1.9 Hz, 1H), 7.15 (d, J=2.0 Hz, 2H), 7.08 (dd, J=8.9 Hz, 2.0 Hz, 1H), 6.92 (s, 1H), 6.68 (s, 1H), 4.17-4.01 (m, 3H), 3.82 (s, 6H), 2.77-2.59 (m, 2H), 1.08 (s, 9H). Analysis Calcd for C$_{24}$H$_{29}$NO$_6$: C, 67.43; H, 6.84; N, 3.28. Found: C, 67.59; H, 6.73; N, 3.39.

3',5'-Dimethoxy-7-[2-hydroxy-3-iso-propylamino-propoxy]-flavone (44)

3',5'-Dimethoxy-7-(2,3-epoxy-propoxy)-flavone, 32 (700 mg, 2 mmol) and iso-propyl amine (1.0 mL, 12 mmol) in dry methanol (120 mL) were reacted in a similar manner to that described under 34 to afford 44. Yield 720 mg (87%); mp 155-156° C.; MS (FAB) 414 (M$^+$+1); IR (KBr) 3426, 1630; $^1$H NMR (200 MHz, DMSO-d$_6$) δ 7.95 (d, J=8.9 Hz, 1H), 7.34 (s, 1H), 7.18 (d, J=1.8 Hz, 2H), 7.09 (dd, J=8.9 Hz, 1.9 Hz, 1H), 6.96 (s, 1H), 6.70 (s, 1H), 4.20-3.90 (m, 3H), 3.85 (s, 6H), 2.84-2.58 (m, 3H), 1.03 (d, J=6.2 Hz, 6H). Analysis Calcd for C$_{23}$H$_{27}$NO$_6$: C, 66.81; H, 6.58; N, 3.39. Found: C, 66.69; H, 6.13; N, 3.62.

3',5'-Dimethoxy-7-[2-hydroxy-3-(4-phenylpiperazin-1-yl)-propoxy]-flavone (45)

3',5'-Dimethoxy-7-(2,3-epoxy-propoxy)-flavone, 32 (400 mg, 1.13 mmol) and 1-phenyl piperazine (0.17 mL, 1.13 mmol) in dry methanol (100 mL) were reacted in a similar manner to that described under 34 to afford 45. Yield 490 mg (84%); mp 195-196° C.; MS (FAB) 517 (M$^+$+1); IR (KBr) 3417, 1633; $^1$H NMR (200 MHz, DMSO-d$_6$) δ 7.97 (d, J=8.8 Hz, 1H), 7.40 (d, J=1.9 Hz, 1H), 7.24 (d, J=1.9 Hz (d, J=7.9 Hz, 2H), 7.12 (dd, J=8.9 Hz, 1.9 Hz, 1H), 7.04 (s, 1H), 6.93 (d, J=8.2 Hz, 2H), 6.80 (d, J=7.1 Hz, 1H), 6.74 (s, 1H), 4.25-4.09 (m, 3H), 3.87 (s, 6H), 3.13 (t, J=6.5 Hz, 4H), 2.63 (d, J=4.5 Hz, 2H), 2.47-2.43 (m, 4H). Analysis Calcd for C$_{30}$H$_{32}$N$_2$O$_6$: C, 69.75; H, 6.24; N, 5.42. Found: C, 69.61; H, 6.53; N, 5.61.

3',4'-Dimethoxy-7-[2-hydroxy-3-iso-propylamino-propoxy]-flavone (46)

3',4'-Dimethoxy-7-(2,3-epoxy-propoxy)-flavone, 33 (300 mg, 0.85 mmol) and iso-propyl amine (0.15 mL, 1.7 mmol) in dry methanol (80 mL) were reacted in a similar manner to that described under 34 to afford 46. Yield 290 mg (83%); mp 144-145° C.; MS (FAB) 414 (M$^+$+1); IR (KBr) 3410, 1634; $^1$H NMR (200 MHz, CDCl$_3$) δ 8.03 (d, J=9.5 Hz, 1H), 7.51 (dd, J=8.5 Hz, 1.7 Hz, 1H), 7.36 (d, J=1.7 Hz, 1H), 6.96-6.92 (m, 3H), 6.74 (s, 1H), 4.18-4.12 (m, 3H), 3.97 (s, 3H), 3.96 (s, 3H), 3.99 (s, (m, 3H), 1.23 (d, J=6.3 Hz, 6H). Analysis Calcd for C$_{23}$H$_{27}$NO$_6$: C, 66.81; H, 6.58; N, 3.39. Found: C, 66.67; H, 6.65; N, 3.53.

3',4'-Dimethoxy-7-[2-hydroxy-3-(4-phenylpiperazin-1-yl)-propoxy]-flavone (47)

3',4'-Dimethoxy-7-(2,3-epoxy-propoxy)-flavone, 33 (300 mg, 0.85 mmol) and 1-phenyl piperazine (0.13 mL, 0.85 mmol) in dry methanol (60 mL) were reacted in a similar manner to that described under 34 to afford 47. Yield 410 mg (94%); mp 191-193° C.; MS (FAB) 517 (M$^+$+1); IR (KBr) 3416, 1627; $^1$H NMR (200 MHz, CDCl$_3$) δ 8.16 (d, J=9.5 Hz, 1H), 7.54 (dd, J=8.3 Hz, 2.1 Hz, 1H), 7.34 (d, J=1.9 Hz, 1H), 7.31-7.23 (m, 2H), 7.04-6.87 (m, 6H), 6.70 (s, 1H), 4.21-4.16 (m, 3H), 3.99 (s, 3H), 3.97 (s, 3H), 3.28 (t, J=4.8 Hz, 4H), 2.90-2.71 (m, 2H), 2.71-2.65 (m, 4H). Analysis Calcd for C$_{30}$H$_{32}$N$_2$O$_6$: C, 69.75; H, 6.24; N, 5.42. Found: C, 69.96; H, 6.57; N, 5.51.

7-(3-tert-Butylamino-2-hydroxy-propoxy)-3',5'-dihydroxy-flavone (48)

To a suspension of 7-(3-tert-butylamino-2-hydroxy-propoxy)-3',5'-dibenzyloxy-flavone, 34 (1.0 g, 1.73 mmol) in dry methanol (60 mL) was added 40 mg 10% Pd/C. The reaction mixture was shaken in Parr hydrogenation assembly under hydrogen gas atmosphere at 60 lbs for 4 h after replacement of the air by nitrogen. The Pd/C was filtered and methanol evaporated on rotavapor under reduced pressure to provide 48. Yield 660 mg (96%); mp 153° C. (decomposes); MS (FAB) 400 (M$^+$+1); IR (KBr) 3401, 1618; $^1$H NMR (200 MHz, DMSO-d$_6$) δ 7.98 (d, J=8.8 Hz, 1H), 7.30 (s, 1H), 7.13 (d, J=8.8 Hz, 1H), 6.90 (d, J=1.2 Hz, 2H), 6.7 (s, 1H), 6.52 (s, 1H), 4.27-4.23 (m, 3H), 3.18-2.99 (m, 2H), 1.32 (s, 9H). Analysis Calcd for C$_{22}$H$_{25}$NO$_6$: C, 66.15; H, 6.31; N, 3.51. Found: C, 66.19; H, 6.47; N, 3.43.

3',5'-Dihydroxy-7-(2-hydroxy-3-iso-propylamino-propoxy)-flavone (49)

3',5'-Dibenzyloxy-7-(2-hydroxy-3-iso-propylamino-propoxy)-flavone, 35 (1.2 g, 2.12 mmol) was debenzylated in dry methanol (40 mL) with 10% Pd/C (30 mg) under hydrogen atmosphere as described for 48 to provide 49. Yield 800 mg (98%); mp 185° C. (decomposes); MS (FAB) 386 (M$^+$+1); IR (KBr) 3244, 1623; $^1$H NMR (200 MHz, DMSO-d$_6$) δ 9.85 (s, 2H), 7.72 (d, J=8.8 Hz, 1H), 7.06 (d, J=1.7 Hz, 1H), 6.87 (dd, J=8.8 Hz, 1.9 Hz, 1H), 6.66 (d, J=1.7 Hz, 2H), 6.45 (s, 1H), 6.29 (s, 1H), 4.00-3.97 (m, 3H), 3.13-3.03 (m, 1H), 2.94-2.75 (m, 2H), 1.24 (d, J=5.7 Hz, 6H); $^{13}$C NMR δ 176.7, 163.3, 163.1, 159.3, 157.7, 133.2, 126.6, 117.6, 115.4, 106.9, 106.3, 104.6, 101.9, 70.9, 65.3, 50.3, 46.9, 19.0, 18.6. Analysis Calcd for C$_{21}$H$_{23}$NO$_6$: C, 65.44; H, 6.02; N, 3.63. Found: C, 66.26; H, 6.18; N, 3.44.

7-(3-tert-Butylamino-2-hydroxy-propoxy)-3',4'-dihydroxy-flavone (50)

7-(3-tert-Butylamino-2-hydroxy-propoxy)-3',4'-dibenzyloxy-flavone, 37 (1.4 g, 2.4 mmol) was debenzylated in dry methanol (40 mL) with 10% Pd/C (30 mg) under hydrogen atmosphere as described for 48 to provide 50. Yield 930 mg (97%); mp 165° C. (decomposes); MS (FAB) 400 (M$^+$+1); IR (KBr) 3274, 1623; $^1$H NMR (200 MHz, DMSO-d$_6$) δ 7.95 (d, J=8.8 Hz, 1H), 7.47 (s, 1H), 7.44 (d, J=9.4 Hz, 1H), 7.29 (s, 1H), 7.10 (d, J=8.8 Hz, 1H), 6.95 (d, J=8.1 Hz, 1H), 6.68 (s, 1H), 4.28-4.19 (m, 3H), 3.18-3.14 (m, 1H), 2.97-2.94 (m, 1H), 1.34 (s, 9H). Analysis Calcd for C$_{22}$H$_{25}$NO$_6$: C, 66.15; H, 6.31; N, 3.51. Found: C, 66.26; H, 6.27; N, 3.27.

3',4'-Dihydroxy-7-(2-hydroxy-3-iso-propylamino-propoxy)-flavone (51)

3',4'-Dibenzyloxy-7-(2-hydroxy-3-iso-propylamino-propoxy)-flavone, 38 (1.0 g, 1.77 mmol) was debenzylated in dry methanol (40 mL) with 10% Pd/C (30 mg) under hydrogen atmosphere as described for 48 to provide 51. Yield 600 mg (88%); mp 187° C. (decomposes); MS (FAB) 386 (M$^+$+1); IR (KBr) 3425, 1624; $^1$H NMR (200 MHz, DMSO-d$_6$) δ 7.96 (d, J=7.1 Hz, 1H), 7.47 (s, 1H), 7.45 (d, J=8.2 Hz, 1H), 7.30 (s, 1H), 7.10 (d, J=8.1 Hz, 1H), 6.95 (d, J=7.6 Hz, 1H), 6.68 (s, 1H), 4.23-4.18 (m, 3H), 3.21-3.18 (m, 3H), 1.27 (d, J=6.2 Hz, 6H). Analysis Calcd for C$_{21}$H$_{23}$NO$_6$: C, 65.44; H, 6.02; N, 3.63. Found: C, 65.37; H, 6.18; N, 3.47.

6-(3-tert-Butylamino-2-hydroxy-propoxy)-3',4'-dihydroxy-flavone (52)

6-(3-tert-Butylamino-2-hydroxy-propoxy)-3',4'-dibenzyloxy-flavone, 39 (1.16 g, 2 mmol) was debenzylated in dry methanol (40 mL) with 10% Pd/C (30 mg) under hydrogen atmosphere as described for 48 to provide 52. Yield 740 mg (93%); mp 193° C. (decomposes); MS (FAB) 400 (M$^+$+1); IR (KBr) 3399, 1616; $^1$H NMR (200 MHz, DMSO-d$_6$) δ 7.93 (s, 1H), 7.55 (d, J=9.5 Hz, 1H), 7.53 (s, 1H), 7.39 (d, J=9.8 Hz, 1H), 7.34 (d, J=8.5 Hz, 1H), 6.93 (d, J=8.0 Hz, 1H), 6.62 (s, 1H), 4.41-4.12 (m, 3H), 3.07-2.93 (m, 2H), 1.33 (s, 9H). Analysis. Calcd for C$_{22}$H$_{25}$NO$_6$: C, 66.15; H, 6.31; N, 3.51. Found: C, 66.26; H, 6.47; N, 3.61.

4-(Thiazolidin-2,4-dione-5-ylidinemethyl)-phenol (55)

A mixture of 4-hydroxy benzaldehyde, 53 (3 g, 24.6 mmol), 2,4-thiazolidinedione, 54 (2.9 g, 24.8 mmol), pipieridine (2.5 mL) and methanol (100 mL) was refluxed for 18 h. The reaction mixture was poured into water and acidified with acetic acid to give 55, which was recrystallised from methanol. Yield 4.7 g (86%); mp 296-298° C.; MS (FAB) 222 (M$^+$+1); IR (KBr) 3404, 3123, 1723, 1678; $^1$H NMR (200 MHz, DMSO-d$_6$) δ 7.70 (s, 1H), 7.46 (d, J=8.6 Hz, 2H), 6.93 (d, J=8.6 Hz, 2H).

7-(2-Bromo-ethoxy)-3',5'-dibenzyloxy-flavone (56)

Potassium carbonate (2.76 g, 20 mmol) was added to a stirred solution of 3',5'-dibenzyloxy-7-hydroxy-flavone, 22 (2.25 g, 5 mmol) in dry dimethyl formamide (120 mL). After the mixture was stirred for 30 min, dibromo ethane (5 mL, 58 mmol) was added and the resultant was stirred at room temperature for 12 h. Reaction mixture was filtered through celite, concentrated under reduced pressure and extracted with chloroform. The extract was washed with water, dried over sodium sulphate, filtered and concentrated in vacuo. The residue was purified by column chromatography to afford 56. Yield 2.6 g (93%); mp 157-159° C.; MS (FAB) 557/559 (M$^+$+1); IR (KBr) 1640; $^1$H NMR (200 MHz, CDCl$_3$) δ 8.13 (d, J=8.8 Hz, 1H), 7.43-7.34 (m, 10H), 7.10 (d, J=2.1 Hz, 2H), 6.99 (dd, J=8.8 Hz, 2.2 Hz, 1H), 6.93 (d, J=2.1 Hz, 1H), 6.76 (s, 1H), 6.69 (s, 1H), 5.10 (s, 4H), 4.39 (t, J=6.2 Hz, 2H), 3.69 (t, J=6.2 Hz, 2H).

7-(2-Bromo-ethoxy)-3',4'-dibenzyloxy-flavone (57)

This compound (57) was prepared from 3',4'-dibenzyloxy-7-hydroxy-flavone, 23 (2.3 g, 5.1 mmol), dibromo ethane (1.7 mL, 20.4 mmol) and potassium carbonate (3.5 g, 25.5 mmol) in dry dimethyl formamide (90 mL) using the identical procedure as described for 56. Yield 2.1 g (74%); mp 167-168° C.; MS (FAB) 557/559 (M$^+$+1); IR (KBr) 1626; $^1$H NMR (200 MHz, CDCl$_3$) δ 8.12 (d, J=8.8 Hz, 1H), 7.50-7.32 (m, 12H), 7.01 (d, J=9.1 Hz, 1H), 6.92 (dd, J=8.9 Hz, 2.2 Hz, 1H), 6.91 (s, 1H), 6.60 (s, 1H), 5.24 (s, 4H), 4.39 (t, J=6.2 Hz, 2H), 3.69 (t, J=6.3 Hz, 2H).

7-(2-Bromo-ethoxy)-3',4',5'-trimethoxy-flavone (58)

This compound (58) was prepared from 7-hydroxy-3',4',5'-trimethoxy-flavone, 25 (2.3 g, 7 mmol), dibromo ethane (3 mL, 35 mmol) and potassium carbonate (2.9 g, 21 mmol) in dry dimethyl formamide (120 mL) using the identical procedure as described for 56. Yield 2.1 g (68%); mp 184-185° C.;

MS (FAB) 435/437 (M++1); IR (KBr) 1631; $^1$H NMR (200 MHz, CDCl$_3$) δ 8.15 (d, J=9.3 Hz, 1H), 7.10 (s, 2H), 7.01 (d, J=7.8 Hz, 1H), 6.99 (s, 1H), 6.71 (s, 1H), 4.43 (t, J=6.2 Hz, 2H), 3.96 (s, 6H), 3.93 (s, 3H), 3.70 (t, J=6.2 Hz, 2H).

7-(3-Bromo-propoxy)-3',4',5'-trimethoxy-flavone (59)

This compound (59) was prepared from 7-hydroxy-3',4', 5'-trimethoxy-flavone, 25 (3.3 g, 10 mmol), dibromo propane (3 mL, 30 mmol) and potassium carbonate (2.7 g, 20 mmol) in dry dimethyl formamide (120 mL) using the identical procedure as described for 56. Yield 3.1 g (69%); mp 156-157° C.; MS (FAB) 449/451 (M++1); IR (KBr) 1629; $^1$H NMR (200 MHz, CDCl$_3$) δ 8.13 (d, J=9.4 Hz, 1H), 7.11 (s, 2H), 7.01-6.97 (m, 2H), 6.70 (s, 1H), 4.25 (t, J=5.8 Hz, 2H), 3.96 (s, 6H), 3.93 (s, 3H), 3.64 (t, J=6.3 Hz, 2H), 2.39 (q, J=6.1 Hz, 2H).

7-(3-Bromo-propoxy)-3',5'-dimethoxy-flavone (60)

This compound (60) was prepared from 3',5'-dimethoxy-7-hydroxy-flavone, 26 (1.1 g, 3.7 mmol), dibromo propane (1.9 mL, 18.5 mmol) and potassium carbonate (1.5 g, 11.1 mmol) in dry dimethyl formamide (100 mL) using the identical procedure as described for 56. Yield 1.1 g (74%); mp 173-174° C.; MS (FAB) 419/421 (M++1); IR (KBr) 1631; $^1$H NMR (200 MHz, DMSO-d$_6$) δ 7.88 (d, J=8.8 Hz, 1H), 7.35 (d, J=2.1 Hz, 1H), 7.17 (d, J=2.1 Hz, 2H), 7.02 (dd, J=8.9 Hz, 2.2 Hz, 1H), 6.98 (s, 1H), 6.66 (s, 1H), 4.19 (t, J=5.9 Hz, 2H), 3.79 (s, 6H), 3.64 (t, J=6.4 Hz, 2H), 2.26 (q, J=6.2 Hz, 2H).

7-(3-Bromo-propoxy)-3',4'-dimethoxy-flavone (61)

This compound (61) was prepared from 3',4'-dimethoxy-7-hydroxy-flavone, 27 (3 g, 10 mmol), dibromo propane (4 mL, 39.2 mmol) and potassium carbonate (2.8 g, 20 mmol) in dry dimethyl formamide (150 mL) using the identical procedure as described for 56. Yield 3.4 g (80%); mp 148-149° C.; MS (FAB) 419/421 (M++1); IR (KBr) 1630; $^1$H NMR (200 MHz, CDCl$_3$) δ 8.12 (d, J=9.5 Hz, 1H), 7.53 (dd, J=8.5 Hz, 2.0 Hz, 1H), 7.36 (d, J=1.9 Hz, 1H), 6.99-6.95 (m, 3H), 6.68 (s, 1H), 4.24 (t, J=5.8 Hz, 2H), 3.98 (s, 3H), 3.96 (s, 3H), 3.64 (t, J=6.3 Hz, 2H), 2.39 (q, J=6.1 Hz, 2H).

3',5'-Dibenzyoxy-7-{2-[4-(thiazolidin-2,4-dione-5-ylidinemethyl)-phenoxy]-ethoxy}-flavone (62)

A mixture of 7-(2-bromo-ethoxy)-3',5'-dibenzyloxy-flavone, 56 (2 g, 3.6 mmol), 4-(thiazolidin-2,4-dione-5-ylidinemethyl)-phenol, 55 (1.2 g, 5.4 mmol) and potassium carbonate (740 mg, 5.4 mmol) in dry dimethyl formamide (120 mL) were stirred at room temperature for 8 h. The reaction mixture was filtered through celite, diluted with water and acidified with dilute hydrochloric acid and filtered. The crude product was purified by column chromatography to yield 62. Yield 600 mg (24%); mp 267-269° C.; MS (FAB) 698 (M++1); IR (KBr) 3451, 1736, 1696, 1618; $^1$H NMR (200 MHz, DMSO-d$_6$) δ 7.92 (d, J=8.9 Hz, 1H), 7.73 (s, 1H), 7.55 (d, J=8.7 Hz, 2H), 7.49-7.32 (m, 12H), 7.29 (s, 1H), 7.17 (s, 2H), 7.05 (d, J=8.0 Hz, 1H), 7.03 (s, 1H), 6.89 (s, 1H), 5.19 (s, 4H), 4.49 (s, 2H), 4.47 (s, 2H). Analysis Calcd for C$_{41}$H$_{31}$NO$_8$S: C, 70.57; H, 4.48; N, 2.01; S, 4.60. Found: C, 70.16; H, 4.52; N, 2.02; S, 4.23.

3',4'-Dibenzyloxy-7-{2-[4-(thiazolidin-2,4-dione-5-ylidinemethyl)-phenoxy]-ethoxy}-flavone (63)

A mixture of 7-(2-bromo-ethoxy)-3',4'-dibenzyloxy-flavone, 57 (2 g, 3.6 mmol), 4-(thiazolidin-2,4-dione-5-ylidinemethyl)-phenol, 55 (1.5 g, 6.8 mmol) and potassium carbonate (1.4 g, 10 mmol) in dry dimethyl formamide (120 mL) were reacted in a similar way as described for 62 to yield 63. Yield 300 mg (12%); mp 239-241° C.; MS (FAB) 698 (M++1); IR (KBr) 3446, 1734, 1674, 1627; $^1$H NMR (200 MHz, DMSO-d$_6$) δ 10.35 (s, 1H), 7.87 (d, J=8.9 Hz, 1H), 7.82 (s, 1H), 7.69 (s, 1H), 7.64 (d, J=8.6 Hz, 1H), 7.44 (d, J=8.3 Hz, 2H), 7.49-7.33 (m, 10H), 7.27 (d, J=2.6 Hz, 1H), 7.18 (d, J=8.6 Hz, 1H), 6.97 (dd, J=8.8 Hz, 2.2 Hz, 1H), 6.88 (d, J=8.5 Hz, 2H), 6.87 (s, 1H), 5.23 (s, 2H), 5.21 (s, 2H), 4.37 (s, 2H), 4.05 (s, 2H). Analysis Calcd for C$_{41}$H$_{31}$NO$_8$S: C, 70.57; H, 4.48; N, 2.01; S, 4.60. Found: C, 70.46; H, 4.63; N, 2.17; S, 4.19.

7-{2-[4-(thiazolidin-2,4-dione-5-ylidinemethyl)-phenoxy]-ethoxy}-3',4',5'-trimethoxy-flavone (64)

A mixture of 7-(2-bromo-ethoxy)-3',4',5'-trimethoxy-flavone, 58 (2 g, 4.6 mmol), 4-(thiazolidin-2,4-dione-5-ylidinemethyl)-phenol, 55 (1.1 g, 5 mmol) and potassium carbonate (2.5 g, 18 mmol) in dry dimethyl formamide (150 mL) were reacted in a similar way as described for 62 to yield 64. Yield 380 mg (14%); mp 237-238° C.; MS (FAB) 576 (M++1); IR (KBr) 3423, 1733, 1681, 1630; $^1$H NMR (300 MHz, DMSO-d$_6$) δ 10.37 (s, 1H), 7.92 (d, J=9.0 Hz, 1H), 7.86 (s, 1H), 7.49 (d, J=9.0 Hz, 2H), 7.38 (d, J=3.0 Hz, 1H), 7.36 (s, 2H) 7.06 (s, 1H), 7.02 (dd, J=9.0 Hz, 3.0 Hz, 1H), 6.91 (d, J=9.0 Hz, 2H), 4.41 (t, J=4.5 Hz, 2H), 4.11 (t, J=4.5 Hz, 2H), 3.91 (s, 6H), 3.75 (s, 3H). Analysis Calcd for C$_{30}$H$_{25}$NO$_9$S: C, 62.60; H, 4.38; N, 2.43; S, 5.57. Found: C, 62.67; H, 4.41; N, 2.37; S, 5.55.

7-{3-[4-(thiazolidin-2,4-dione-5-ylidinemethyl)phenoxy]-propoxy}-3',4',5'-trimethoxy-flavone (65)

A mixture of 7-(3-bromo-propoxy)-3',4',5'-trimethoxy-flavone, 59 (3 g, 6.7 mmol), 4-(thiazolidin-2,4-dione-5-ylidinemethyl)-phenol, 55 (1.7 g, 7.7 mmol) and potassium carbonate (3.7 g, 27 mmol) in dry dimethyl formamide (150 mL) were reacted in a similar way as described for 62 to yield 65. Yield 900 mg (23%); mp 203-204° C.; MS (FAB) 590 (M++1); IR (KBr) 3401, 1733, 1683, 1626; $^1$H NMR (300 MHz, DMSO-d$_6$) δ 10.33 (s, 1H), 7.88 (d, J=9.0 Hz, 1H), 7.77 (s, 1H), 7.45 (d, J=9.0 Hz, 2H) 7.32 (s, 1H), 7.28 (d, J=3.0 Hz, 1H), 7.03 (s, 1H), 6.96 (dd, J=9.0 Hz, 3.0 Hz, 1H), 6.93 (d, J=9.0 Hz, 2H), 4.18 (t, J=7.5 Hz, 2H), 3.88 (s, 6H), 3.85 (t, J=7.5 Hz, 2H), 3.73 (s, 3H), 2.12-2.09 (m, 2H); $^{13}$C NMR (200 MHz, DMSO-d$_6$) δ 176.9, 168.0, 166.3, 163.3, 162.4, 160.4, 157.7, 153.6, 140.9, 133.7, 132.9, 126.8, 126.4, 124.2, 117.4, 117.1, 116.7, 115.0, 106.9, 104.2, 101.9, 66.9, 60.6, 56.6, 26.9. Analysis Calcd for C$_{31}$H$_{27}$NO$_9$S: C, 63.15; H, 4.62; N, 2.38; S, 5.44. Found: C, 63.41; H, 4.39; N, 2.61; S, 5.29.

3',5'-Dimethoy-7-{3-[4-(thiazolidin-2,4-dione-5-ylidinemethyl)-phenoxy]-propoxy}-flavone (66)

A mixture of 7-(3-bromo-propoxy)-3',5'-dimethoxy-flavone, 60 (1 g, 2.4 mmol), 4-(thiazolidin-2,4-dione-5-ylidinemethyl)-phenol, 55 (600 mg, 2.7 mmol) and potassium carbonate (1.3 g, 9.4 mmol) in dry dimethyl formamide (80 mL) were reacted in a similar way as described for 62 to yield 66. Yield 220 mg (16%); mp 229-230° C.; MS (FAB) 560 (M$^+$+1); IR (KBr) 3229, 1733, 1678, 1632; $^1$H NMR (300 MHz, DMSO-d$_6$) δ 10.34 (s, 1H), 7.88 (d, J=9.0 Hz, 1H), 7.79 (s, 1H), 7.47 (d, J=6.0 Hz, 2H), 7.30 (s, 1H), 7.20 (s, 2H), 7.02 (s, 1H), 6.98 (d, J=9.0 Hz, 1H), (d, J=6.0 Hz, 2H), 6.71 (s, 2H), 4.20 (s, 2H), 3.84 (s, 2H), 3.84 (s, 6H), 2.14-2.12 (m, 2H). Analysis Calcd for C$_{30}$H$_{25}$NO$_8$S: C, 64.39; H, 4.50; N, 2.50; S, 5.73. Found: C, 64.26; H, 4.33; N, 2.61; S, 6.05.

3',4'-Dimethoxy-7-{3-[4-(thiazolidin-2,4-dione-5-ylidinemethyl)-phenoxy]-propoxy}-flavone (67)

A mixture of 7-(3-bromo-propoxy)-3',4'-dimethoxy-flavone, 61 (2.5 g, 6 mmol), 4-(thiazolidin-2,4-dione-5-ylidinemethyl)-phenol, 55 (1.4 g, 6.33 mmol) and potassium carbonate (1 g, 7.24 mmol) in dry dimethyl formamide (120 mL) were reacted in a similar way as described for 62 to yield 67. Yield 600 mg (18%); mp 240-241° C.; MS (FAB) 560 (M$^+$+1); IR (KBr) 3429, 1738, 1679, 1622; $^1$H NMR (200 MHz, DMSO-d$_6$) δ 10.38 (s, 1H), 7.91 (d, J=8.8 Hz, 1H), 7.82 (s, 1H), 7.64 (d, J=9.0 Hz, 1H), 7.59 (s, 1H), 7.50 (d, J=8.6 Hz, 2H), 7.25 (d, J=1.9 Hz, 1H), 7.12 (d, J=8.6 Hz, 1H), 6.99 (d, J=8.8 Hz, 1H), 6.96 (s, 1H), 6.94 (d, J=8.5 Hz, 2H), 4.22 (s, 4H), 3.90 (s, 3H), 3.87 (s, 3H), 2.25 (s, 2H). Analysis Calcd for C$_{30}$H$_{25}$NO$_8$S: C, 64.39; H, 4.50; N, 2.50; S, 5.73. Found: C, 64.66; H, 4.71; N, 2.59; S, 5.64.

Biological Screening

The biological screening of the synthesized compounds for antihyperglycemic and antidyslipidemic activities were carried out in Biochemistry Division, Central Drug Research Institute. Sucrose loaded rat model was used for primary screening followed by streptozotocin induced beta cell damaged diabetic model of Sprague Dawley strain male albino rat model. The compounds, which exhibited significant activity repeatedly in STZ model, were subjected to screen in db/db mice. The serum of the mice was also analyzed for lipid profile of the compounds exhibiting antihyperglycemic activity. All the compounds were also screened for antidyslipidemic activity in triton model.

Evaluation of Antihyperglycemic Activity

Sucrose Loaded Rat Model (SLM)

Male albino rats of Charles Foster/Wistar strain of average body weight 160±20 g were selected for this study. The blood glucose level of each animal was checked by glucometer using glucostrips (Boehringer Mannheim) after 16 h starvation. Animals showing blood glucose levels between 3.33 to 4.44 mM (60 to 80 mg/dl) were divided into groups of five to six animals in each. Animals of experimental group were administered suspension of the desired synthetic compound orally (made in 1.0% gum acacia) at a dose of 100-mg/kg-body weight. Animals of control group were given an equal amount of 1.0% gum acacia. A sucrose load (10.0 g/kg) was given to each animal orally exactly after 30 min post administration of the test sample/vehicle. Blood glucose profile of each rat was again determined at 30, 60, 90 and 120 min post administration of sucrose by glucometer. Food but not water was withheld from the cages during the course of experimentation. Quantitative glucose tolerance of each animal was calculated by Area Under Curve (AUC) method (Prism Software). Comparing the AUC of experimental and control groups determined the percentage antihyperglycemic activity. Statistical comparison was made by Dunnett's test.

Sucrose-challenged Streptozotocin-induced Diabetic Rats (STZS)

Male albino rats of Sprague Dawley strain of body weight 160+20 g were selected for this study. Streptozotocin (Sigma, USA) was dissolved in 100 mM citrate buffer pH 4.5 and calculated amount of the fresh solution was injected to overnight fasted rats (45 mg/kg) intraperitoneally. Blood glucose level was checked 48 h later by glucostrips and animals showing blood glucose values between 144 to 270 mg/dl (8 to 15 mM) were included in the experiment and termed diabetic. The diabetic animals were divided into groups consisting of five to six animals in each group. Animals of experimental groups were administered suspension of the desired test samples orally (made in 1.0% gum acacia) at a dose of 100-mg/kg-body weight. Animals of control group were given an equal amount of 1.0% gum acacia. A sucrose load of 2.5-g/kg body weight was given after 30 minutes of compound administration. After 30 minutes of post sucrose load blood glucose level was again checked by glucostrips at 30, 60, 90, 120, 180, 240, 300 min and at 24 h, respectively. Animals not found diabetic after 24 hours post treatment of the test sample were not considered and omitted from the calculations and termed as non-responders. The animals, which did not show any fall in blood glucose profile in a group while the others in that group, showed fall in blood glucose profile were also considered as non-responders. Food but not water was withheld from the cages during the experimentation. Comparing the AUC of experimental and control groups determined the percent antihyperglycemic activity. Statistical comparison between groups was made by Student's 't' test.

$$\% \text{ Antihyperglycemic Activity} = 100 - \frac{\text{Average blood glucose level of test substance treated group at test time}}{\text{Average blood glucose level of control group at test time}} \times 100$$

Evaluation of Antidyslipidemic Activity

Triton Model

Male Charles foster rats weighing 200-225 g were divided into control, hyperlipidemic and hyperlipidemic plus drug treated groups containing six animals in each group. Hyperlipidemia was induced by administration of triton WR-1339 (200 mg/kg i.p.). All animals were maintained on a special pellet diet and water ad libitum. Compounds and standard drug were macerated with 0.2% aqueous gum acacia suspension. The suspension was fed orally at the dose of 100 mg/kg simultaneously with triton in drug treated group. The animals of control group received the same amount of gum acacia by similar route of administration. At the end of the experiment, after 18 h, blood was withdrawn from retro orbital plexus and plasma was used for the assay of total cholesterol, phospholipid and triglycerides.

Lipid Estimation

Cholesterol

Cholesterol was estimated using the kit provided by Roche Diagnostics. Cholesterol esters are enzymatically hydrolyzed by cholesterol esterase (CE) to cholesterol and free fatty acids. Free cholesterol, including that originally present, is then oxidized by cholesterol oxidase (CO) to cholest-4-en-3-one and hydrogen peroxide. The hydrogen peroxide combines with hydroxy benzoic acid (HBA) and 4-aminoantipyrine (4AAA) in the presence of peroxidase (POD) to form a chromophore (quinoneimine dye), which may be quantitated at 500-505 nm. The intensity of red colour formed is directly proportional to the concentration of total cholesterol in the specimen and measured spectrophotometrically (Searcy, C. L. Diagnostic Biochemistry, 1969, McGraw Hill, New York; Ellefson, R. D.; Caraway, W. T. Fundamentals of clinical chemistry, 1976, Ed Tietz N W, 506-515.)

Triglycerides

Triglycerides were estimated using the kit provided by Roche Diagnostics. Lipoprotein lipase hydrolyses triglycerides to yield glycerol and fatty acids. Glycerol kinase converts glycerol to glycerol-3-phosphate, which is oxidized by glycerol phosphate oxidase to dihydroxy acetone phosphate and hydrogen peroxide. In the presence of peroxidase, hydrogen peroxide oxidatively couples with 4-aminoantipyrine and 4-chloro phenol to produce red quinonimine dye. The intensity of red colour formed is directly proportional to the concentration of triglycerides in the specimen and is measured by photometrically (Wahlefeld, A. W.; Bergmeyer, H. U. Ed. Methods of enzymatic analysis, $2^{nd}$ English edition, New York, N.Y., Academic press inc, 1831-1840.).

Phospholipids

Serum (0.2 mL) and perchloric acid (1.0 mL) was digested at 180° C. for 1-1.5 h till the solution became colorless. The liberated inorganic phosphate (Pi) was measured by the method of Fiske and Subbarow (Fiske, C. H.; Subbarow, V. *J. Biol. Chem.* 1925, 66, 375.). 1 mL of 2.5% ammonium molybdate (prepared in 5 N sulphuric acid) and 0.5 mL reducing agent (4-amino naphthol sulphonic acid, 0.2%), sodium metabisulphite (2.4% w/v in distilled water) was added to the above tubes and mixed well. The reaction mixture was distilled with 2.5 mL of triple distilled water and kept at 60° C. in water bath for 20 min. For standard, an appropriate amount of potassium dihydrogen phosphate dissolved in triple distilled water containing 2-10 μg phosphorous (Pi) was run simultaneously with the experiment tubes. The optical density of the blue colour was recorded at 620 nm against reagent blank. The values of Pi were converted into phospholipid by multiplying with 25 (a constant calibrated from Pi value of lecithin).

TABLE 3

Antihyperglycemic and antidyslipidemic activity in SLM, STZ-S and triton models

| Compd. No. | % Fall in blood glucose levels (SLM&STZ-S models) | | | % Fall in lipid levels (Triton model) | | |
|---|---|---|---|---|---|---|
| | SLM | STZ-S 5 h | 24 h | TC | PL | TG |
| 34 | 29.4 | 21.6** | 28.7** | 21 | 18 | 9 |
| 35 | NIL | ND | ND | 13 | 8 | 11 |
| 36 | 34.6 | NIL | 2.46 | 24 | 21 | 17 |
| 37 | NIL | ND | ND | 23 | 12 | 16 |
| 38 | NIL | ND | ND | 16 | 5 | 14 |
| 39 | 21.83 | 14.9 | 0.36 | 21 | 12 | 17 |
| 40 | NIL | ND | ND | 24 | 26 | 28 |
| 41 | 20.72 | 17.4 | 19.1 | 18 | 16 | 19 |
| 42 | 5.64 | ND | ND | 19 | 8 | 23 |
| 43 | NIL | ND | ND | 21 | 19 | 17 |
| 44 | 1.36 | ND | ND | 17 | 21 | 24 |
| 45 | NIL | ND | ND | 30 | 20 | 31 |
| 46 | 23.95 | ND | ND | ND | ND | ND |
| 47 | 5.45 | ND | ND | 23 | 22 | 19 |
| 48 | 19.1 | NIL | NIL | 17 | 4 | 16 |
| 49 | 29.0 | 26.9** | 13.2* | 32 | 28 | 32 |

TABLE 3-continued

Antihyperglycemic and antidyslipidemic activity in SLM, STZ-S and triton models

| Compd. No. | % Fall in blood glucose levels (SLM&STZ-S models) | | | % Fall in lipid levels (Triton model) | | |
|---|---|---|---|---|---|---|
| | SLM | STZ-S 5 h | 24 h | TC | PL | TG |
| 50 | NIL | ND | ND | 21 | 23 | 25 |
| 51 | NIL | ND | ND | 15 | 13 | 19 |
| 52 | 4.96 | ND | ND | 24 | 23 | 25 |
| 62 | NIL | ND | ND | 15 | 15 | 18 |
| 63 | 26.0 | ND | ND | — | — | — |
| 64 | 9.59 | ND | ND | 20 | 25 | 26 |
| 65 | 29.30 | 16.1 | 11.0 | 20 | 6 | 3 |
| 66 | 28.80 | 18.9 | 20.2 | — | — | — |
| 67 | 13.60 | 18.7 | 13.6 | 28 | 14 | 21 |

Evaluation of Antihyperglycemic and Antidyslipidemic Activity in db/db Mice

The db/db mouse is a well-characterized model of type II diabetes. The background for the db/db mouse is the C57BL/Ks strain. The major deficiency of the C57BL/KsBom-db mouse (db/db) is lack of a functional leptin receptor. This leads to defective leptin signaling and a complete lack of feedback from leptin. Both hypothalamic NPY content and secretion are consequently elevated, and this result in hyperphagia and decreased energy expenditure, obesity, insulin-resistance, hyperinsulinaemia, hyperglycemia and dyslipidemia. The db/db mouse develops NIDDM from around week 10. The disease is stable until week 20, where destruction of pancreatic β-cells can be recognized clinically as decreasing levels of plasma insulin and very severe hyperglycemia. The male mice are more diabetic than female and will normally die earlier. The advantage of using male mice for experimental purposes is that the fluctuations in plasma parameters are less than in the females where the estrogen cycles affects the clinical diabetes mellitus. The optimal age of db/db mice used for experiments will be from week 12 to 18 when they have developed NIDDM with diabetic dyslipidemia but still have functional β-cells in the pancreas. C57BL/KsBom-db mice 12-18 weeks, 40-50 g bred in the animal house of CDRI, Lucknow. 10 male mice were used in the experiments. The mice were housed in groups of 5 individuals in a room controlled for temperature (23+2° C.) and 12/12 hours light/dark cycle (lights on at 6.00 am). Body weight was measured daily from day 1 to day 10. All animals had free access to fresh water and to normal chow except on the days of the postprandial protocol day 6 and during the overnight fast before the OGTT on day 10. Blood glucose was checked every morning up till day 5. On day 6 postprandial protocol was employed, in this method blood glucose was checked at −0.30 min and 0 h. Test compounds were given to the treatment group whereas control group received only gum acacia (1.0%); the blood glucose was again checked at 1, 2, 3, 4 and 6 h post test compound treatment. Finally on day 10 an oral glucose tolerance test (OGTT) was performed after an overnight fasting. Blood glucose was measured at −0.30 min and test drugs were fed, blood glucose was again measured at 0.0 min post treatment, at this juncture glucose solution was given at a dose of 3 gm/kg to all the groups including control group; the profile of blood glucose was checked at 30 min, 60 min, 90 min and 120 min post glucose administration. Quantitative glucose tolerance of each animal was calculated by Area Under Curve (AUC) method (Prism Software). Comparing the AUC of experimental and control groups determined the percentage antihyperglycemic activity. Statistical comparison was made by Dunnett's test.

Lipid Estimation

Cholesterol and triglycerides were estimated using the same procedures as given above.

HDL-Cholesterol

HDL-Cholesterol was estimated using the kit provided by the Roche Diagnostics. Cholestest N HDL is a liquid reagent that directly measures the HDL-cholesterol concentration in serum by a new method that is based on the selective solubilising effect of proprietary detergent to the different lipoproteins. In the assay system, only HDL is solubilised by a special detergent; other lipoproteins are not disrupted. After HDL is selectively disrupted, HDL cholesterol is measured enzymatically (Gordon, T.; Casstelli, W. P.; Hjortland, M. C.; Kannel, W. B.; Dawber, T. R. High density lipoproteins as a protective factor against coronary heart disease, Am. J. Med. 1977, 62, 707-714.).

TABLE 4

Antihyperglycemic activity in db/db mice

| Compound number | % Fall in blood glucose levels | |
|---|---|---|
| | 6 days | 10 days |
| 34 | 26.4 | 57.1 |
| 49 | 9.38 | 20.5 |
| 65 | 19.1 | 21.4 |

TABLE 5

Antidyslipidemic activity in db/db mice

| Compound number | % Fall in lipid levels | | |
|---|---|---|---|
| | TG | Chol. | HDL |
| 34 | 33.5 | +26.9 | +19.3 |
| 49 | 24.1 | 17.2 | +12.7 |
| 65 | 19.1 | 1.06 | 35.2 |

Dose Dependent Antihyperglycemic Effect of 34 on Sucrose Challenged Streptozotocin-induced Diabetic Rats As depicted in the FIGURE, a dose response curve of 34 was obtained by administering different doses of test compound to streptozotocin-induced diabetic rats (Table 6). Doses ranged from 50-250 mg/kg were given and blood glucose level was measured at 30, 60, 90, 120, 180, 240, 300 and 1440 min post administration of sucrose load as described in sucrose-challenged challenged streptozotocin-induced diabetic rats. Compound 34 showed dose dependency and its $ED_{50}$ was found to be 90 mg/kg.

TABLE 6

Dose dependent antihyperglycemic effect of 34 on sucrose challenged streptozotocin-induced diabetic rats

| Exp. No. | Dose | % Fall in blood glucose levels | |
|---|---|---|---|
| | | 5 h | 24 h |
| 1 | 25 | 11.1 | 13.6 |
| 2 | 50 | 9.62 | 13.8 |
| 3 | 100 | 19.8 | 21.9 |
| 4 | 150 | 24.3 | 30.5 |

TABLE 6-continued

Dose dependent antihyperglycemic effect of 34 on sucrose challenged streptozotocin-induced diabetic rats

| Exp. No. | Dose | % Fall in blood glucose levels | |
|---|---|---|---|
| | | 5 h | 24 h |
| 5 | 200 | 38.1 | 37.0 |
| 6 | 250 | 40.7 | 45.5 |

Results:

The majority of the compounds exhibited significant antihyperglycemic activity in SLM as well as STZ model. Out of which two most active compounds 34 and 49 were screened in db/db mice. The compound 34 lowered glucose level by 26.4% on $6^{th}$ day and 57.1% on $10^{th}$ day where as compound 49 lowered glucose levels by 9.38% and 20.8% respectively. Thus compound with lipophilic substitution on hydroxy function and its 1,3-positioning in B-ring had high activity compared to non-lipophilic substitution and 1,2-dihydroxy substitution. Compound 34 also had significant lowering of triglyceride (−33.5%) with simultaneous rise of reverse cholesterol transport profile, HDL-C by +19.3% in db/db mice (Table 3, 4 and 5). Compound 34 was also studied for dose dependency in STZ-S model and its $ED_{50}$ was found to be 90 mg/kg (Table 6).

Compound 65 belong to thiazolidinedione series and exhibited significant and consistent glucose lowering activity in SLM and STZ models and subjected for test in db/db mice and lowered glucose levels 19.1% and 21.4% on $6^{th}$ and $10^{th}$ day respectively (Table 3, 4, 5). It lowered the triglycerides by 19.1%.

Pharmacological Data of Compounds 34 & 49

In order to know whether compounds 34 & 49 have any effect on central nervous system some specific tests like gross behaviour, maximal electroshock seizures (MES), barbiturate hypnosis were performed. However the compound is devoid of any CNS effect.

Animals

Swiss adult (10-12 weeks old) mice of either sex, weighing 20-25 g bred in Division of Laboratory Animals, CDRI were used in the study.

Housing of Animals

Each group of mice was kept in acrylic cages. The standard food pellets and water (through a glass bottle fitted with a nozzle) was available for 24 h except during the period of observation. The animals were kept in an air-conditioned laboratory (room temperature maintained between 22-26° C.) with 12 h light and dark cycle.

Dose and Route of Administration

The test substance 34 and 49 was administered by oral route in dose 100 mg/kg as aqueous suspension with gum acacia. One group received the vehicle to serve as control.

The effect of 34 and 49 was studied on following responses:

a. Mortality
b. Gross behaviour
c. Maximal electroshock seizures (MES)
d. Barbiturate hypnosis Mortality 34 and 49 in dose of 100 mg/kg, p.o. did not cause any mortality up to 14 days (n=10).

b). Gross Behavioural Responses

The study on gross behavioural responses indicates the effect of test substance on neuromuscular, sensory and autonomic nervous system of the mice.

Experimental Procedures 34 and 49 (100 mg/kg, p.o.) was administered in forenoon. Mice of control and treated groups (n=10) were observed at 30 min intervals up to 3 h after administration.

The gross behavioral parameters were observed as follows (based on Irwin protocol):

1). Motor Responses
i). Spontaneous motor activity [SMA]: Scored on a scale of 0-9 in which SMA in control group was assigned score 4.
ii). Posture/Position: Normal upright posture (+: present or –: absent)
iii). Gait: The mouse is allowed to move on the edge of the cage for 1 min and straight movements without fall or staggering is considered as normal. The gait is recorded as normal or abnormal; if abnormal description is provided.
iv). Ataxia: Any in-coordination in movements occurring in absence of involuntary movements. (+: present or –: absent)
v). Tremor: Involuntary movements (jerking of entire body or limbs) due to alternating contraction of muscles. (+: present or –: absent)
vi). Convulsions: Alternate contraction (flexion) and extension [clonic], or sustained extension [tonic] of limbs resulting into loss of upright posture (+: present or –: absent).
vii). Straub's tail: A sustained (>30 sec) raising of tail (making an angle >60° with the body) (+: present or –: absent)
viii). Catalepsy: A condition in which body or limbs remain passively in any position in which they are placed. It is tested by the placing forepaws on a metallic rod placed at height of 6 cm and if forepaws are not withdrawn within 10 sec catalepsy is considered to be positive (+: present or –: absent).
ix). Abnormal (Bizarre) behaviour: Stereotypy, head shaking, head searching, upright walking, and circling (+: present or –: absent).

Results

No obvious change in spontaneous locomotor activity was observed during upto 180 min. (Table 7).

TABLE 7

SMA Score in control and treated groups

| | Time interval (min) after drug administration | | | | | | |
|---|---|---|---|---|---|---|---|
| Exp | 0 | 30 | 60 | 90 | 120 | 150 | 180 |
| Control | 4 | 4 | 4 | 4 | 4 | 4 | 4 |
| 34 | 4 | 4 | 4 | 4 | 4 | 4 | 4 |
| 49 | 4 | 4 | 4 | 4 | 4 | 4 | 4 |

There was no effect on gait and posture.
No abnormal (bizarre) behavior was observed.

Inference 34 and 49 in doses of 100 mg/kg did not show any significant effect on motor responses.

2). Autonomic Responses
i). Piloerection: Erection of body hairs (+: present or –: absent)
ii). Salivation: Secretion of saliva is observed as dripping of saliva from mouth, which is scored as 1=mild, 2=moderate and 3=severe as compared to control (0=no dripping).
iii). Lachrymation: Secretion and discharge of tears observed as shedding of tears around the lower eyelid, which is scored as 1=mild, 2=moderate and 3=severe as compared to control (0=no shedding).
iv). Palpebral closure: Ptosis (drooping of upper eyelids) present or absent
v). Exopthalmos: Protrusion (bulging) of eye ball; present or absent
vi). Defaecation: scored as 1=mild, 2=moderate and 3=severe as compared to control
vii). Urination: scored as 1=mild, 2=moderate and 3=severe as compared to control Results Autonomic responses-secretions and ophthalmic signs were normal in 34 and 49 treated mice as compared to control.

Inference 34 and 49 in dose of 100 mg/kg, p.o. did not show any significant effect on autonomic responses.

3). Sensory
i). Reflexes: Pinna, corneal and righting reflexes were tested [Normal (control), sluggish or absent]
ii). Nociceptive Response: Reaction time to nociceptive response was observed by hot plate analgesia meter (Columbus Instruments,USA). The cut-off period for thermal nociception (55° C.) to mice was 15 sec.

Results i). Reflexes: Corneal, pinna and righting reflexes were intact in 34 and 49 treated mice.
ii). Nociceptive Response: 34 and 49 in dose of 100 mg/kg, p.o. showed no significant effect on nociceptive reaction time as compared to control (Table 8).

TABLE 8

Nociceptive reaction time (Sec) MEAN ± SE

| | Time interval (min) after drug administration | | | | |
|---|---|---|---|---|---|
| Exp. | Pre-tt (0) | 30 | 60 | 90 | 120 |
| Control | 3.64 ± 0.1 | 3.84 ± 0.2 | 4.22 ± 0.6 | 3.51 ± 0.3 | 3.20 ± 0.1 |
| 34 | 3.52 ± 0.2 | 4.84 ± 0.3 | 4.30 ± 0.2 | 3.52 ± 0.1 | 3.08 ± 0.2 |
| 49 | 4.61 ± 0.2 | 4.66 ± 0.6 | 4.10 ± 0.2 | 3.66 ± 0.3 | 3.45 ± 0.1 |

No Significant difference from control value (one way ANOVA followed by Bonferroni test)

Inference

Sensory responses are not affected by 34 and 49 in doses of 100 mg/kg p.o.

4). Neuromuscular Coordination
i). Muscle Tone
By resistance to passive flexion of each hind-paw
Score: 0=Flaccid, 1=Normal, 2=Rigid,
ii). Rota Rod Test
The period of stay on rotating rod (speed: 5 rotations/min; total duration of test 2 min) for each control and treated mice (–60 min) was recorded by Rotamex 4 (Columbus Instr., USA). The mice were trained to stay for period of 2 min on rotating rod and only trained mice were included in the study.

Results i). Muscle Tone
All the mice in control as well as treated with both the doses of 34 and 49 showed normal hind limb rigidity (score 1).

ii). Rota Rod Test

Control (vehicle), 34 and 49 showed fall of 1 mice at only 1 h post treatment otherwise control and treated mice did not show any fall i.e. stayed upto 2 min on the rod in rota-rod test (5 rounds/min for 2 min) at other time intervals (Table 9a&b).

TABLE 9a

Rota rod test-numbers of falls

| Exp. | Time interval (min) | | | | |
|---|---|---|---|---|---|
| | Pre-tt (0) | 30 | 60 | 90 | 180 |
| Vehicle | 0 | 0 | 1/8 | 0 | 0 |
| 34 | 0 | 0 | 1/8 | 0 | 0 |
| 49 | 0 | 0 | 1/8 | 0 | 0 |

TABLE 9b

Rota rod test-stay period

| Exp. | Stay period at 1 h in seconds (MEAN ± SE) |
|---|---|
| Vehicle | 114.91 ± 5.12 |
| 34 | 111.87 ± 8.82 |
| 49 | 112.25 ± 7.75 |

Inference 34 and 49 in doses of 100 mg/kg, p.o. did not show any significant effect on Neuromuscular coordination as compared to control.

c). Maximal Electroshock Seizures (MES)

Control and treated mice (−60 min) were subjected to electric shock (48 mAmp for 0.2 sec) through pinna electrode. All the mice showed tonic seizures (Table 10).

TABLE 10

Maximal electroshock seizures (MES)

| Exp. | Numbers of mice showed seizures/ numbers of mice tested |
|---|---|
| Vehicle | 5/5 |
| 34 | 5/5 |
| 49 | 5/5 |

Inference 34 and 49 in dose of 100 mg/kg, p.o. did not show any significant anti-convulsant activity.

d). Barbiturate Induced Hypnosis

Barbiturate Sleeping Time

Sleeping time is calculated by the duration between loss and regain of righting reflex following administration of Pentobarbitone (45 mg/kg, i.p.). 34 and 49 in the dose 100 mg/kg, p.o. was administered 30 min prior to Pentobarbitone.

Results 34 and 49 did not affect significantly Pentobarbitone (45 mg/kg, i.p.) induced sleep (Table 11).

TABLE 11

Barbiturate induced hypnosis

| Exp. | Sleep-duration (min) (MEAN ± SE) |
|---|---|
| Vehicle | 92.8 ± 8.6 |
| 34 | 122.5 ± 16.7 |
| 49 | 103.4 ± 15.27 |

No significant change from control value (one way ANOVA followed by Bonferroni test)

Inference 34 and 49 in dose of 100 mg/kg, p.o. did not show any significant change in barbiturate induced hypnosis.

Summary of Pharmacological Data

Compound 34 and 49 in dose of 100 mg/kg, p.o.:
Non-lethal upto 14 days,
No significant persistent effect on gross behavior,
No anti-convulsant activity,
No significant influence on barbiturate hypnosis.
No significant sedative (no suppression of SMA, reflexes, sensory response, neuromuscular coordination rota rod test and MES) or stimulant (absence of marked increase in SMA, no convulsions, tremors or stereotypy) activity,
Therefore, it appears that the compounds 34 and 49 in 100 mg/kg, p.o. dose are devoid of any major CNS effects.

We claim:

1. A compound having a formula (34) or a pharmaceutically acceptable salt thereof:

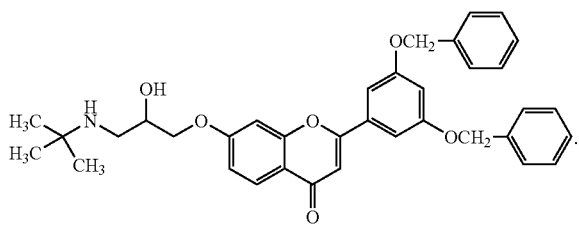

2. A compound having a formula (49) or a pharmaceutically acceptable salt thereof:

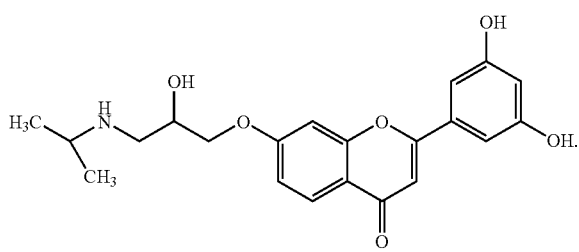

* * * * *